United States Patent [19]

Chan

[11] Patent Number: 5,798,209
[45] Date of Patent: Aug. 25, 1998

[54] HUMAN AND MOUSE VERY LOW DENSITY LIPOPROTEIN RECEPTORS AND METHODS FOR USE OF SUCH RECEPTORS

[75] Inventor: Lawrence C. B. Chan, Houston, Tex.

[73] Assignee: Baylor College of Medicine, Houston, Tex.

[21] Appl. No.: 451,883

[22] Filed: May 26, 1995

Related U.S. Application Data

[62] Division of Ser. No. 149,103, Nov. 8, 1993.

[51] Int. Cl.$^6$ .................... C12Q 1/68; C12P 19/34; C07H 21/04; C07H 21/02
[52] U.S. Cl. .................... 435/6; 536/23.1; 536/24.3; 536/24.33; 435/91.2
[58] Field of Search .................... 536/23.1, 24.3–24.33; 435/6, 91.2

[56] References Cited

U.S. PATENT DOCUMENTS 4,870,009  9/1989  Evans et al. ........................... 435/70
4,873,316  10/1989  Meade et al. ........................... 530/412

OTHER PUBLICATIONS

Takahashi et al. PNAS 89: 9252–9256, 1992.
Nora and Fraser, in Medical Genetics: Principles and Practices, Lea and Febiger, pp. 120–129, 1989.
Sakai et al. Genebank Sequence Listing, 1993.
Beisiegel et al., "Lipoprotein Lipase Enhances the Binding of Chylomicrons to Low Density Lipoprotein Receptor–Related Protein," 88 *Proc. Natl. Acad. Sci. USA* 8342, 1991.
Blankenhorn et al., "Beneficial Effects of Combined Colestipol–Niacin Therapy on Coronary Atherosclerosis and Coronary Venous Bypass Grafts," 257 *JAMA* 3233, 1987.
Brown et al., "Regression of Coronary Artery Disease as a Result of Intensive Lipid–Lowering Therapy in Men with Hight Levels on Apolipoprotein B," 323 *N. Engl. J. Med.* 1289, 1990.
Burns et al., "Vesicular Stomatitis Virus G Glycoprotein Pseudotyped Retroviral Vectors: Concentration to Very High titer and Efficient Gene Transfer into Mammalian and Nonmammalian Cells," 90 *Proc. Natl. Acad. Sci. USA* 8033, 1993.
Chan et al., "Molecular Genetics of the Plasma Apolipoproteins," In: Molecular Biology of the Cardiovascular System, Chien ed., Lea & Febiger, Philadelphia, London, pp. 183–219, 1990 vol. # not applicable.
Chappell et al., "The Low Density Lipoprotein Receptor–Related Protein/$\alpha_2$–Macroglobulin Receptor Binds and Mediates Catabolism of Bovine Milk Lipoprotein Lipase," 267 *J. Biol. Chem.* 25764, 1992.
Chen et al., "NPXY, a Sequence Often Found in Cytoplasmic Tails, is Required for Coated Pit–Mediated Internalization of the Low Density Lipoprotein Receptor," 265 *J. Biol. Chem.* 3116, 1990.
Chowdhury et al. "Long–Term Improvement of Hypercholesterolemia After Ex Vivo Gene Therapy in LDLR–Deficient Rabbits," 254 *Science* 1802, 1991.

Cristiano et al, "Hepatic Gene Therapy: Adenovirus Enhancement of Receptor–Mediated Gene Delivery and Expression in Primary Hepatocytes," 90 *Proc. Natl. Acad. Sci. USA* 2122, 1993.
Curiel et al., "Adenovirus Enhancement of Transferrin–Polylysine–Mediated Gene Delivery," 88 *Proc. Natl. Acad. Sci. USA* 8850, 1991.
Davis et al., "Acid–Dependent Ligand Dissociation and Recycling of LDL Receptor Mediated by Growth Factor Homology Region," 326 *Nature* 760, 1987.
Denmacker et al., "Increased Removal of $\beta$–Very Low Density Lipoproteins after Ethinyl Estradiol is Associated with Increased mRNA Levels for Hepatic Lipase, Lipoprotein Lipase, and the Low Density Lipoprotein Receptor in Watanabe Heritable Hyperlipidemic Rabbits," 11(6) *Arteriosclerosis and Thrombosis* 1652, 1991.
Eisenberg et al., "Lipoprotein Lipase Enhances Binding of Lipoproteins to Hepran Sulfate on Cell Surfaces and Extracellular Matrix," 90 *J. Clin. Invest.* 2013, 1992.
Esser et al., "Mutational Analysis of the Ligand Binding Domain of the Low Density Lipoprotein Receptor," 263 *J. Biol. Chem.* 13282, 1988.
Goldstein et al., "Receptor–Mediated Endocytosis of Low–Density Lipoprotein in Cultured Cells," 98 *Methods Enzymol.* 241, 1983.
Chan, "Genes, Dyslipoproteinemia and Coronary Artery Disease."In: Treatment of Severe Hypercholesterolemia in the Prevention of Coronary Heart Disease—Gotto et al. (eds), Proc 2nd Int Symp Munich 1989, Basel, Karger, pp. 1–11, 1990 vol. 2.
Graham and Prevec, "Manipulation of Adenovirus Vectors," 7 *Methods in Molecular Biology* 109–128, E.J. Murray, ed., Humana Press, NJ, 1991.
Grossman et al., "Transplantation of Genetically Modified Autologous Hepatocytes into Nonhuman Primates: Feasibility and Short–Term Toxicity," 3(5) *Human Gene Therapy* 501, 1992.
Kamps et al., "Complete Down–Regulation of Low–Density Lipoprotein Receptor Activity in Human Liver Parenchymal Cells by $\beta$–very–low–density Lipoprotein," 287 *FEBS* 34, 1991.
Kane et al., "Normalization of Low–Density–Lipoprotein Levels in Heterozygous Familial Hypercholesterolemia with a Combined Drug Regimen," 304 *N. Engl. J. Med.* 251, 1981.

(List continued on next page.)

*Primary Examiner*—W. Gary Jones
*Assistant Examiner*—Dianne Rees
*Attorney, Agent, or Firm*—Lyon & Lyon LLP

[57] ABSTRACT

Methods of treating diseases or conditions, characterized by elevated serum lipoprotein levels, by providing elevated levels of a VLDL receptor in an animal, e.g., a human are set forth. Such receptors aid in removal of circulating VLDL and related lipoproteins, and thus decrease the risk of developing coronary diseases or conditions or decrease the severity of such diseases or conditions. Clones of human and mouse VLDL receptor which can be used in the invention are also provided. Vectors for the expression of VLDL receptors, stably transfected and transformed cells and transgenic animals are also provided.

3 Claims, 6 Drawing Sheets

OTHER PUBLICATIONS

Kaneda et al., "The Improved Efficient Method for Introducing Macromolecules into Cells Using HVJ (Sendai Virus) Liposomes with Gangliosides," 173 *Expt. Cell Res.* 56, 1987.

Kaneda et al., "Increased Expression of DNA Cointroduced with Nuclear Protein in Adult Rat Liver," 243 *Science* 375, 1989.

Lee et al., "Nucleotide Sequence of the Rat Low Density Lipoprotein Receptor cDNA," 17(3) *Nucleic Acids Research* 1259, 1989.

Lindgren et al., "Human Genes Involved in Cholesterol Metabolism: Chromosomal Mapping of the Loci for the Low Density Lipoprotein Receptor and 3–hydroxy–3–methylglutarly–coenzyme A Reductase with cDNA Probes," 82 *Proc. Natl. Acad. Sci. USA* 8567, 1985.

van den Maagdenberg et al., "Transgenic Mice Carrying the Apolipoprotein E3–Leiden Gene Exhibit Hyperlipoproteinemia," 268(14) *J. Biol. Chem.* 10540, 1993.

Maniatis, Fritsch and Sambrook, Molecular Cloning: A Laboratory Manual. Cold Spring Harbor Laboratory, Cold Spring Harbor, NY, 1982 vol. #, pp. #' not applic.

Mehta et al., "The Low Density Lipoprotein Receptor in *Xenopus laevis*," 266(16) *J. Biol. Chem.* 10415, 1991.

Miller, "Retrovirus Packaging Cells," *1 Hum. Gene Ther.* 5, 1990.

Morgan and Anderson, "Human Gene Therapy," 62 *Annu. Rev. Biochem.* 191, 1993.

Mulder et al., "Low Density Lipoprotein Receptor Internalizes Low Density and Very Low Density Lipoproteins that are Bound to Heparan Sulfate Proteoglycans via Lipoprotein Lipase, " 268 *J. Biol. Chem.* 9369, 1993.

Rumsey et al., "Lipoprotein Lipase–Mediated Uptake and Degradation of Low Density Lipoproteins by Fibroblasts and Macrophages," 90 *J. Clin. Invest.* 1504, 1992.

Russell et al., "Different Combinations of Cysteine–Rich Repeats Mediate Binding of Low Density Lipoprotein Receptor to Two Different Proteins," 264 *J. Biol. Chem.* 21682, 1989.

Takahashi et al., "Rabbit Very Low Density Lipoprotein Receptor: A Low Density Lipoprotein Receptor–Like Protein with Distinct Ligand Specificity," 89 *Proc. Natl. Acad. Sci. USA* 9252, 1992.

Williams "Gene Therapy for Ischemic Heart Disease: Current Prospects," 5(1) *J. Myocardial Ischemia* 13, 1993.

Williams et al., "Mechanisms by Which Lipoprotein Lipase Alters Cellular Metabolism of Lipoprotein(a), Low Density Lipoprotein, and Nascent Lipoproteins," 267 *J. Biol. Chem.* 13284, 1992.

Wislow et al., "Ex Vivo Gene Therapy of Familial Hypercholesterolemia," 3(2) *Human Gene Therapy* 179, 1992.

Wolff et al., "Direct Gene Transfer into Mouse Muscle In Vivo," 247 *Science* 1465, 1990.

Wu et al., "Receptor–Mediated Gene Delivery In Vivo. Partial Correction of Genetic Analbuminemia in Nagaes Rats," 266 *J. Biol. Chem.* 14338, 1991.

Wu and Wu, "Receptor–Mediated In Vitro Gene Transformation by a Soluble DNA Carrier System," 262 *J. Biol. Chem.* 4429, 1987.

Yamamoto et al., "The Human LDL Receptor: A Cysteine–Rich Protein with Multiple Alu Sequences in its mRNA," 39 *Cell* 27, 1984.

Yamamoto et al., "Deletion in Cysteine–Rich Region of LDL Receptor Impedes Transport to Cell Surface in WHHL Rabbit," 232 *Science* 1230, 1986.

Yang et al., "Human Very Low Density Lipoprotein Structure: Interaction of the C Apolipoproteins with Apolipoprotein B–100," 34 *J. Lipid Research* 1311, 1993.

Yokode et al., "Diet–Induced Hypercholesterolemia in Mice: Prevention by Overexpression of LDL Receptors," 250 *Science* 1273, 1990.

Zhu et al., "Systemic Gene Expression After Intravenous DNA Delivery into Adult Mice," 261 *Science* 209, 1993.

NCEP Adult Treatment Panel II Report, "Summary of the Second Report of the National Cholesterol Education Program (NCEP) Expert Panel on Detection, Evaluation, and Treatment of High Blood Cholesterol in Adults (Adult Treatment Panel II)," 269 *JAMA* 3015, 1993.

Anderson, "Gene Therapy: Several Hundred Patients Have Already Received Treatment. In the Next Century the Procedure will be Commonplace," *Scientific American* pp. 124–128 (Sep. 1995) (vol. # not applicable).

Datta et al., "Human Hepatic Lipase—Cloned cDNA Sequence, Restriction Fragment Length Polymorphisms, Chromosomal Localization, and Evolutionary Relationships with Lipoprotein Lipase and Pancreatic Lipase," *J. Biol. Chem.* 263:1107–1110 (1988).

Engelberg, "Heparin and atherosclerosis. A review of old and recent findings," *American Heart Journal* 99:359–372 (1990).

Gafvels et al., "Cloning of a cDNA Encoding Putative Human Very Low Density Lipoprotein/Apolipoprotein E Receptor and Assignment of the Gene to Chromosome 9pter–p236," *Somatic Cell and Molecular Genetics* 19:557–569 (1993).

Herz and Gerard, "Adenovirus–mediated transfer of low density lipoprotein receptor gene acutely accelerates cholesterol clearance in normal mice," *Proc. Natl. Acad. Sci. USA* 90:2812–2816 (1993).

Hodgson, "The Vector Void in Gene Therapy," *Bio/Technology* 13:222–225 (1995).

Hoffer et al., "The Mouse Low Density Lipoprotein Receptor Gene: cDNA Sequence and Exon–Intron Structure,"*Biochemical and Biophysical Research Communications* 191:880–886 (1993).

Hofmann et al., "Overexpression of Low Density Lipoprotein (LDL) Receptor Eliminates LDL from Plasma in Transgenic Mice," *Science* 239:1277–1281 (1988).

Ishibashi et al., "Hypercholesterolemia in Low Density Lipoprotein Receptor Knockout Mice and Its Reversal by Adenovirus–mediated Gene Delivery," *J. Clin. Invest.* 92:883–893 (1993).

Kappel et al., "Regulating gene expression in transgenic animals," *Current Opinion in Biology* 3:548–553 (1992).

Lusis, "The Mouse Model for Atherosclerosis," *Trends in Cardiovascular Surgery* 3:135–143 (1993).

Miller, "Pharmacotherapy of Disorders of Plasma Lipoprotein Metabolism," *American Journal of Cardiology* 66:16A–19A (1990).

Mulligan, "The Basic Science of Gene Therapy," *Science* 260:926–932 (1993).

Oka et al., "Human Very–Low–Density Lipoprotein Receptor Complementary DNA and Deduced Amino Acid Sequence and Localization of Its Gene (VLDLR) to Chromosome Band 9p24 by Fluorescence in Situ Hybridization," *Genomics* 20:298–300 (1994).

Oka et al., "Mouse very–low–density–lipoprotein receptor (VLDLR) cDNA cloning, tissue–specific expression and evolutionary relationship with the low–density–lipoprotein receptor," *Eur. J. Biochem.* 224:975–982 (1994).

Orkin and Motulsky, *Report and Recommendations of the Panel to Assess the NIH Investment in Research on Gene Therapy*, Dec. 7, 1995.

Strojek and Wagner, "The Use of Transgenic Animal Techniques for Livestock Improvement," in *Genetic Engineering: Principles and Methods*, vol. 10, Plenum Press, pp. 221–246 (1988).

Turley and Dietschy, "Ch. 34—The Metabolism and Excretion of Cholesterol by the Liver," in *The Liver: Biology and Pathology*, 2nd edition, edited by Arias et al., Raven Press, Ltd., New York, pp. 617–641 (1988).

Webb et al., "Characterization and tissue–specific expression of the human 'very low density lipoprotein (VLDL) receptor' mRNA,"*Human Molecular Genetics* 3:531–537 (1994).

Williams, "Gene Therapy for Ischemic Heart Disease: Current Prospects," *J. Myocardial Ischemmia* 5:13–22 (1993).

Fig. 1A

```
TTTCCCCTCCCCGCCCCCACCTTCTTCCTCCTTTCGGAAGGGCTGGTAACTTGTTGTGCG
GAGCGAACGGCGGCGGCGGCGGCGGCGGCGGCACCATCCAGGCGGGCACCATGGGCA
CGTCCGCGCTCTGGGCGCTCTGGCTGCTCGTCGCGCTGTGCTGGGCGCCCCGGGAGAGCG
GCGCCACCGGAACCGGGAGAAAAGCCAAATGTGAACCCTCCCAATTCCAGTGCACAAATG
GTCGCTGTATTACGCTGTTGTGGAAATGTGATGGGGATGAAGACTGTGTTGACGGCAGTG
ATGAAAAGAACTGTGTAAAGAAGACGTGTGCTGAATCTGACTTCGTGTGCAACAATGGCC
AGTGTGTTCCCAGCCGATGGAAGTGTGATGGAGATCCTGACTGCGAAGATGGTTCAGATG
AAAGCCCAGAACAGTGCCATATGAGAACATGCCGCATACATGAAATCAGCTGTGGCGCCC
ATTCTACTCAGTGTATCCCAGTGTCCTGGAGATGTGATGGTGAAAATGATTGTGACAGTG
GAGAAGATGAAGAAAACTGTGGCAATATAACATGTAGTCCCGACGAGTTCACCTGCTCCA
GTGGCCGCTGCATCTCCAGGAACTTTGTATGCAATGGCCAGGATGACTGCAGCGATGGCA
GTGATGAGCTGGACTGTGCCCCGCCAACCTGTGGCGCCCATGAGTTCCAGTGCAGCACCT
CCTCCTGCATCCCCATCAGCTGGGTATGCGACGATGATGCAGACTGCTCCGACCAATCTG
ATGAGTCCCTGGAGCAGTGTGGCCGTCAGCCAGTCATACACACCAAGTGTCCAGCCAGCG
AAATCCAGTGCGGCTCTGGCGAGTGCATCCATAAGAAGTGGCGATGTGATGGGGACCCTG
ACTGCAAGGATGGCAGTGATGAGGTCAACTGTCCCTCTCGAACTTGCCGACCTGACCAAT
TTGAATGTGAGGATGGCAGCTGCATCCATGGCAGCAGGCAGTGTAATGGTATCCGAGACT
GTGTCGATGGTTCCGATGAAGTCAACTGCAAAAATGTCAATCAGTGCTTGGGCCCTGGAA
AATTCAAGTGCAGAAGTGGAGAATGCATAGATATCAGCAAAGTATGTAACCAGGAGCAGG
ACTGCAGGGACTGGAGTGATGAGCCCCTGAAAGAGTGTCATATAAACGAATGCTTGGTAA
ATAATGGTGGATGTTCTCATATCTGCAAAGACCTAGTTATAGGCTACGAGTGTGACTGTG
CAGCTGGGTTTGAACTGATAGATAGGAAAACCTGTGGAGATATTGATGAATGCCAAAATC
CAGGAATCTGCAGTCAAATTTGTATCAACTTAAAAGGCGGTTACAAGTGTGAATGTAGTC
GTGGCTATCAAATGGATCTTGCTACTGGCGTGTGCAAGGCAGTAGGCAAAGAGCCAAGTC
TGATCTTCACTAATCGAAGAGACATCAGGAAGATTGGCTTAGAGAGGAAAGAATATATCC
AACTAGTTGAACAGCTAAGAAACACTGTGGCTCTCGATGCTGACATTGCTGCCCAGAAAC
TATTCTGGGCCGATCTAAGCCAAAAGGCTATCTTCAGTGCCTCAATTGATGACAAGGTTG
GTAGACATGTTAAAATGATCGACAATGTCTATAATCCTGCAGCCATTGCTGTTGATTGGG
TGTACAAGACCATCTACTGGACTGATGCGGCTTCTAAGACTATTTCAGTAGCTACCCTAG
ATGGAACCAAGAGGAAGTTCCTGTTTAACTCTGACTTGCGAGAGCCTGCCTCCATAGCTG
TGGACCCACTGTCTGGCTTTGTTTACTGGTCAGACTGGGGTGAACCAGCTAAAATAGAAA
AAGCAGGAATGAATGGATTCGATAGACGTCCACTGGTGACAGCGGATATCCAGTGGCCTA
ACGGAATTACACTTGACCTTATAAAAAGTCGCCTCTATTGGCTTGATTCTAAGTTGCACA
TGTTATCCAGCGTGGACTTGAATGGCCAAGATCGTAGGATAGTACTAAAGTCTCTGGAGT
TCCTAGCTCATCCTCTTGCACTAACAATATTTGAGGATCGTGTCTACTGGATAGATGGGG
AAAATGAAGCAGTCTATGGTGCCAATAAATTCACTGGATCAGAGCTAGCCACTCTAGTCA
ACAACCTGAATGATGCCCAAGACATCATTGTCTATCATGAACTTGTACAGCCATCAGGTA
AAAATTGGTGTGAAGAAGACATGGAGAATGGAGGATGTGAATACCTATGCCTGCCAGCAC
CACAGATTAATGATCACTCTCCAAAATATACCTGTTCCTGTCCCAGTGGGTACAATGTAG
AGGAAAATGGCCGAGACTGTCAAAGTACTGCAACTACTGTGACTTACAGTGAGACAAAAG
ATACGAACTCAACAGAAATTTCAGCAACTAGTGGACTAGTTCCTGGAGGGATCAATGTGA
CCACAGCAGTATCAGAGGTCAGTGTTCCCCCAAAAGGGACTTCTGCCGCATGGGCCATTC
```

Fig. 1B

TTCCTCTCTTGCTCTTAGTGATGGCAGCAGTAGGTGGCTACTTGATGTGGCGGAATTGGC
AACACAAGAACATGAAAAGCATGAACTTTGACAATCCTGTGTACTTGAAAACCACTGAAG
AGGACCTCTCCATAGACATTGGTAGACACAGTGCTTCTGTTGGACACACGTACCCAGCAA
TATCAGTTGTAAGCACAGATGATGATCTAGCTTGACTTCTGTGACAAATGTTGACCTTTG
AGGTCTAAACAAATAATACCCCCGTCGGAATGGTAACCGAGCCAGCAGCTGAAGTCTCTT
TTTCTTCCTCTCGGCTGGAAGAACATCAAGATACCTTTGCGTGGATCAAGCTTGTGTACT
TGACCGTTTTTATATTACTTTTGTAAATATTCTTGTCCACATTCTACTTCAGCTTTGGAT
GTGGTTACCGAGTATCTGTAACCCTTGAATTTCTAGACAGTATTGCCACCTCTGGCCAAA
TATGCACTTTCCCTAGAAAGCCATATTCCAGCAGTGAAACTTGTGCTATAGTGTATACCA
CCTGTACATACATTGTATAGGCCATCTGTAAATATCCCAGAGAACAATCACTATTCTTAA
GCACTTTGAAAATATTTCTATGTAAATTATTGTAAACTTTTTCAATGGTTGGGACAATGG
CAATAGGACAAAACGGGTTACTAAGATGAAATTGCCAAAAAAATTTATAAACTAATTTTG
TACGTATGAATGATATCTTTGACCTCAATGGAGGTTTGCAAAGACTGAGTGTTCAAACTA
CTGTACATTTTTTTTCAAGTGCTAAAAAAT

Fig. 2A

```
CACCATCCGGGCGGGCAGCATGGGCACGTCCGCGCGCTGGGCCCTGTGGCTGCTGCTCG
CGCTGTGCTGGGCGCCCCGGGACAGCGGCGCCACTGCAAGCGGGAAGAAAGCCAAATGT
GATAGCTCCCAGTTTCAGTGCACAAATGGCCGCTGCATTACCCTGCTGTGGAAATGTGA
TGGAGATGAAGACTGTGCGGATGGCAGCGACGAGAAGAACTGTGTAAAGAAGACGTGTG
CTGAGTCTGACTTCGTGTGCAAAAACGGCCAGTGTGTTCCTAACAGATGGCAGTGTGAC
GGGGATCCTGATTGCGAAAACGGTTCTGATGAAAGCCCTGAACAGTGCCATATGAGAAC
ATGCCGCATAAATGAAATCAGCTGTGGCGCCCGTTCTACTCAGTGTATCCCCGTCTCCT
GGAGATGCGATGGTGAAAATGATTGTGACAATGGAGAAGATGAAGAAAACTGTGGCAAC
ATAACATGTAGTGCAGATGAGTTCACTTGCTCCAGTGGCCGCTGCGTCTCCAGAAACTT
TGTGTGCAATGGCCAGGATGACTGTGACGATGGCAGTGATGAGCTGGACTGTGCTCCAC
CAACCTGCGGAGCCCACGAGTTCCAGTGCAGCACCTCTTCCTGCATTCCCCTCAGCTGG
GTGTGTGATGATGACGCAGACTGTTCAGACCAATCAGACGAGTCTCTTGAGCAGTGTGG
CCGTCAGCCTGTGATACATACCAAATGTCCTACCAGTGAGATCCAGTGTGGCTCTGGCG
AGTGCATTCACAAAAAATGGCGGTGTGACGGAGACCCTGACTGCAAGGACGGCAGCGAT
GAGGTCAACTGCCCTTCTCGAACCTGCCGACCTGACCAGTTTGAATGTGAAGATGGTAG
CTGTATCCACGGCAGCAGGCAATGCAATGGCATCCGAGACTGTGTTGATGGCTCTGATG
AAGTCAACTGCAAAAACGTCAATCAGTGCCTGGGCCCTGGAAAGTTCAAGTGCAGAAGC
GGGGAATGCATAGACATGAGCAAAGTATGTGACCAGGAACAAGACTGCAGAGACTGGAG
TGACGAGCCCCTGAAGGAATGCCATATCAACGAATGCCTGGTCAATAATGGTGGCTGTT
CCCATATCTGCAAAGACCTAGTTATAGGTTATGAGTGTGATTGTGCAGCTGGGTTTGAA
CTGATAGATAGGAAAACCTGTGGAGATATTGATGAATGCCAAAACCCGGGGATCTGCAG
TCAAATTTGTATCAACTTAAAAGGCGGTTACAAGTGTGAATGTAGTCGTGGCTATCAAA
TGGATCTTGCCACTGGCGTGTGCAAGGCAGTAGGCAAAGAGCCGAGTCTGATCTTCACT
AATCGAAGAGACATCAGGAAGATTGGCCTAGAGAGAAAGGAATACATCCAACTTGTAGA
GCAACTAAGGAACACGGTGGCTCTCGATGCGGACATTGCAGCTCAGAAGCTGTTTTGGG
CTGATCTCAGCCAGAAGGCCATCTTCAGTGCCTCAATTGATGACAAGGTTGGTAGACAT
TTTAAAATGATCGACAATGTCTATAATCCTGCAGCCATTGCTGTTGATTGGGTGTACAA
GACCATCTACTGGACTGATGCGGCTTCTAAGACTATTTCAGTAGCTACCCTAGACGGAG
CCAAGAGGAAGTTCCTGTTTAATTCTGACTTGCGAGAGCCTGCCTCCATAGCTGTGGAT
CCGTTGTCGGGCTTTGTTTACTGGTCAGACTGGGGCGAGCCAGCTAAAATAGAAAAAGC
AGGAATGAATGGATTTGATAGACGTCCTCTGGTGACGGAGGACATCCAATGGCCTAATG
GAATTACACTCGACCTTGTCAAAAGCCGCCTCTACTGGCTGGATTCCAAGTTGCACATG
CTCTCTAGTGTGGACCTGAATGGTCAAGATCGTAGGATAGTGCTCAAGTCTCTGGAGTT
CCTAGCTCATCCTCTTGCACTCACCATATTTGAGGATCGCGTCTACTGGATAGATGGAG
AAAATGAAGCAGTGTACGGTGCCAATAAATTCACTGGGTCAGAGCTGGCCACTCTAGTG
AATTCCCTCAATGATGCCCAAGACATCATTGTCTACCATGAACTCGTCCAGCCGTCAGG
TAAAAACTGGTGTGAAGACGATATGGAGAATGGAGGATGTGAATATCTCTGCCTGCCAG
CACCACAGATCAATGACCACTCTCCAAAATATACCTGTTCCTGTCCCAATGGGTACAAT
CTCGAAGAAATGGACGAGAGTGTCAAAGTACTTCAACTCCTGTGACTTACAGTGAGAC
AAAAGATATCAACACAACAGACATTCTACGAACTAGTGGACTGGTTCCTGGAGGGATCA
ATGTGACCACAGCAGTATCAGAAGTCAGTGTTCCCCCAAAAGGGACTTCAGCTGCCTGG
GCCATCCTTCCTCTCTTGCTCTTAGTGATGGCAGCAGTAGGTGGCTACTTGATGTGGAG
```

Fig. 2B

GAATTGGCAACATAAAAACATGAAAAGCATGAACTTTGACAATCCTGTGTACTTGAAGA
CCACTGAAGAGGACCTGTCGATAGACATTGGTAGACACAGCGCTTCTGTAGGACACACA
TACCCAGCAATATCAGTTGTAAGCACAGATGATGATCTGGCTTGAGTTCTGAACAAATC
TTGGTCTATGAGGTCTACACCAATAACACCCTACTCTGGAATGGTAACAGAGCCAGCGC
TGAAGTCTCCTTTCTTCCTCCCATCTGGAAGAACATCAAGATATCTTTTTGTGGATCAA
GTTTGAGTACTTGATCATTTTTATATTACTTTTGTAAATATTCTTGGCCACATTCTACT
TCAGCTCTGGATGTGGTTACCAAGTATCTGTAACCCTTGAGCCCCTAGACAGTATTGCC
ATCTCTGGCCAAATATGCACTTTCCCTAGAAAGCCATATTCCAGCAATGAACGTTGTGC
TATAGTGACTCCCACCTGTACATACATTGTATAGGCCACCTGTACATATCCCAGAGAAC
AATCACTATTCTTAAGCACTTTGAAGATATTTCTATGTAAATTATTGTAAACTTTTTCA
ATGGTTGGGACAATGGCAATAGGATAAAACGGGTTACTAAGATGAAAT

Fig. 3

```
GRKAKCEPSQFQCTNGRCITLLWKCDGDEDCVDGSDEKNCVKKTCAESDFVCNNGQCVP
SRWKCDGDPDCEDGSDESPEQCHMRTCRIHEISCGAHSTQCIPVSWRCDGENDCDSGED
EENCGNITCSPDEFTCSSGRCISRNFVCNGQDDCSDGSDELDCAPPTCGAHEFQCSTSS
CIPISWVCDDDADCSDQSDESLEQCGRQPVIHTKCPASEIQCGSGECIHKKWRCDGDPD
CKDGSDEVNCPSRTCRPDQFECEDGSCIHGSRQCNGIRDCVDGSDEVNCKNVNQCLGPG
KFKCRSGECIDISKVCNQEQDCRDWSDEPLKECHINECLVNNGGCSHICKDLVIGYECD
CAAGFELIDRKTCGDIDECQNPGICSQICINLKGGYKCECSRGYQMDLATGVCKAVGKE
PSLIFTNRRDIRKIGLERKEYIQLVEQLRNTVALDADIAAQKLFWADLSQKAIFSASID
DKVGRHVKMIDNVYNPAAIAVDWVYKTIYWTDAASKTISVATLDGTKRKFLFNSDLREP
ASIAVDPLSGFVYWSDWGEPAKIEKAGMNGFDRRPLVTADIQWPNGITLDLIKSRLYWL
DSKLHMLSSVDLNGQDRRIVLKSLEFLAHPLALTIFEDRVYWIDGENEAVYGANKFTGS
ELATLVNNLNDAQDIIVYHELVQPSGKNWCEEDMENGGCEYLCLPAPQINDHSPKYTCS
CPSGYNVEENGRDCQSTATTVTYSETKDTNSTEISATSGLVPGGINVTTAVSEVSVPPK
GTSAAWAILPLLLLVMAAVGGYLMWRNWQHKNMKSMNFDNPVYLKTTEEDLSIDIGRHS
ASVGHTYPAISVVSTDDDLA
```

Fig. 4

GKKAKCDSSQFQCTNGRCITLLWKCDGDEDCADGSDEKNCVKKTCAESDFVCKNGQCVP
NRWQCDGDPDCENGSDESPEQCHMRTCRINEISCGARSTQCIPVSWRCDGENDCDNGED
EENCGNITCSADEFTCSSGRCVSRNFVCNGQDDCDDGSDELDCAPPTCGAHEFQCSTSS
CIPLSWVCDDDADCSDQSDESLEQCGRQPVIHTKCPTSEIQCGSGECIHKKWRCDGDPD
CKDGSDEVNCPSRTCRPDQFECEDGSCIHGSRQCNGIRDCVDGSDEVNCKNVNQCLGPG
KFKCRSGECIDMSKVCDQEQDCRDWSDEPLKECHINECLVNNGGCSHICKDLVIGYECD
CAAGFELIDRKTCGDIDECQNPGICSQICINLKGGYKCECSRGYQMDLATGVCKAVGKE
PSLIFTNRRDIRKIGLERKEYIQLVEQLRNTVALDADIAAQKLFWADLSQKAIFSASID
DKVGRHFKMIDNVYNPAAIAVDWVYKTIYWTDAASKTISVATLDGAKRKFLFNSDLREP
ASIAVDPLSGFVYWSDWGEPAKIEKAGMNGFDRRPLVTEDIQWPNGITLDLVKSRLYWL
DSKLHMLSSVDLNGQDRRIVLKSLEFLAHPLALTIFEDRVYWIDGENEAVYGANKFTGS
ELATLVNSLNDAQDIIVYHELVQPSGKNWCEDDMENGGCEYLCLPAPQINDHSPKYTCS
CPNGYNLEENGRECQSTSTPVTYSETKDINTTDILRTSGLVPGGINVTTAVSEVSVPPK
GTSAAWAILPLLLLVMAAVGGYLMWRNWQHKNMKSMNFDNPVYLKTTEEDLSIDIGRHS
ASVGHTYPAISVVSTDDDLA

HUMAN AND MOUSE VERY LOW DENSITY LIPOPROTEIN RECEPTORS AND METHODS FOR USE OF SUCH RECEPTORS

This application is a divisional of co-pending application Ser. No. 08/149,103 filed Nov. 8, 1993, entitled "Human and Mouse Very Low Density Lipoprotein Receptors and Methods for Use of Such Receptors," the whole of which (including drawings) is hereby incorporated by reference.

BACKGROUND OF THE INVENTION

This invention relates to methods for treatment or prevention of cardiovascular disease.

Cardiovascular disease is the leading cause of death in Western society. A number of factors predispose individuals to premature atherosclerosis, including cigarette smoking, obesity, diabetes mellitus, hypertension, and high plasma cholesterol levels. Atherosclerosis develops when atheromatous plaques form on blood vessels. The lipid deposits in these plaques are derived from circulating plasma lipoproteins. The propensity to develop atherosclerotic cardiovascular disease is directly related to the plasma lipid concentration and distribution, e.g., hyperlipoproteinemia.

The standard treatment modalities for hyperlipoproteinemia include dietary therapy, physical exercise and drug therapy. Dietary therapy occurs in two steps, the Step I and Step II diets, which are designed to progressively reduce intakes of saturated fatty acids (saturated fat) and cholesterol and to promote weight loss in patients who are overweight. Increased physical activity is also an important element in the nonpharmacologic therapy of hyperlipoproteinemia (JAMA 269: 3015–3023, 1993). Currently the drugs recommended for hyperlipoproteinemia can be classified into two classes: Major drugs (bile acid sequestrants, nicotinic acid, and HMGCOA reductase inhibitors); and other drugs (fibric acids and probucol). Bile acid sequestrants are recommended for patients with elevated LDL cholesterol. Nicotinic acid is effective in lowering total cholesterol and triglyceride levels and raising HDL cholesterol levels. Drug therapy is generally used for many years or a lifetime.

An alternative form of therapy is extracorporeal removal of LDL. LDL is removed by some physical means (e.g., adsorption to immunoadsorbant, or dextran sulfate, heparin precipitation, filtration, or plasma exchange). This method has been applied to homozygous familial hypercholesterolemia ("FH") FH patients (Gotto et al., Eds., Treatment of Severe Hypercholesterolemia in the Prevention of Coronary Heart Disease-2, Karger Press, pp.1–11, 1990). It is technically and physically demanding and requires special equipment.

Once atherosclerosis has developed in an artery or arteriole (e.g., a coronary artery), it either progresses, stabilizes or regresses. Regression occurs rarely, although it has been documented and its frequency appears to be increased by aggressive lipid lowering (Blankenhorn et al., JAMA 257: 3233–3240, 1987; Brown et al., N. Engl. J. Med. 323: 1289–1298, 1990; Kane et al., N. Engl. J. Med. 304: 251–258, 1981). Coronary artery stenosis caused by atherosclerosis can be treated by percutaneous transluminal coronary angioplasty or by coronary bypass surgery.

The lipoproteins associated with hyperlipoproteinemia are macromolecular complexes of proteins and lipids (triglycerides, cholesterol and phospholipids) in the circulation. They are classified according to their relative densities: chylomicrons, chylomicron remnants (a metabolic product of chylomicrons), very low density lipoproteins ("VLDL"), intermediate density lipoproteins ("IDL", a metabolic product of VLDL), low density lipoproteins ("LDL", an end product of IDL) and high density lipoproteins ("HDL") The protein components are called apolipoproteins. The major apolipoproteins are apoA-I, A-II, A-IV, B-100, B-48, C-I, C-II, C-III, D, and E. ApoB-100 is present in VLDL, IDL and LDL, whereas apoE is present in chylomicron remnants, VLDL and IDL. High levels of circulating LDL and β-VLDL in blood in particular have been associated with increased risk of cardiovascular heart disease.

ApoB-100 and apoE are ligands for the LDL receptor. Deficiency of the LDL receptor is a cause of familial hypercholesterolemia, an autosomal dominantly heritable disease which results in markedly elevated blood plasma cholesterol levels, and often premature death due to atherosclerosis and resulting myocardial infarction. The administration of a low density lipoprotein receptor gene to attempt to treat familial hypercholesterolemia is discussed in Wilson et al., Human Gene Therapy, 3(2) 179–222 (1992).

SUMMARY OF THE INVENTION

This invention features methods of treating diseases or conditions, characterized by elevated serum lipoprotein levels by elevating levels of a VLDL receptor in an animal, e.g., a human. Such receptors aid in removal of circulating VLDL and related lipoproteins, e.g., from the bloodstream, and thus decrease the risk of developing coronary diseases or conditions or decrease the severity of such diseases or conditions. Clones of human and mouse VLDL receptor which can be used in the invention are also provided.

By "elevated" is meant a serum lipoprotein level above that recognized as within the normal range of levels. "Treating" means lowering the serum lipoprotein level from an abnormally elevated level closer to a normal range of levels, or that the detrimental health effects of an abnormally elevated level of lipoproteins may be diminished or abolished. Examples of diseases or conditions characterized by elevated serum lipoprotein levels are hyperlipidemia, atherosclerosis and hypercholesterolemia. These are only meant as examples and are not meant to be limiting in any way. In addition, the methods of the invention can be used prophylactically, that is, even before an elevated level of various lipoproteins is evident. Thus, the invention has utility in prevention of diseases or conditions to which an individual may be prone.

The VLDL receptor may be expressed only in a specific cell, such as a liver cell (hepatocyte), in which case "elevated" is relative to the normal range of VLDL receptor typically expressed in such liver cells of a particular species or individual within that species. Alternatively or concurrently, the VLDL receptor can be expressed in the blood circulation or blood stream of an animal and in that case "elevated" is relative to the normal range of VLDL receptors typically expressed in the blood stream of a particular species or individual within that species.

The term "elevating" means that VLDL receptor levels above those normally found in such an animal will result from the administration of a VLDL receptor to an animal, or administration of nucleic acid vectors encoding a VLDL receptor through the expression of a nucleic acid sequence contained in the vector. The level of VLDL receptor normally found in any particular animal might be zero.

In a preferred embodiment, an isolated nucleic acid encoding a VLDL receptor, e.g., a human or mouse VLDL receptor, is used to elevate the level of such a receptor within an animal or a cell. Such isolated nucleic acid sequences include a cDNA, genomic DNA clone, RNA or an mRNA species which encode a sequence of a VLDL receptor obtained from a human or mouse and exhibiting some or all of the functional characteristics associated with such a VLDL receptor. Further, any such nucleic acid sequence which encodes a portion of a VLDL receptor which exhibits the functional characteristics of a VLDL receptor as defined herein are within the preferred embodiment. These functional characteristics of a VLDL receptor include but are not limited to the receptors use of apoE as a ligand and its specifically and competeably binding to and internalization, within a cell membrane in which the receptor resides, of the apoE-containing lipoproteins, VLDL, IDL and β-VLDL, but not LDL.

A functional VLDL receptor may encompass any part of the VLDL receptor, alone or as part of a fusion protein, e.g., a VLDL receptor linked through a chemical bond to a part or whole of another protein, so long as it functions as defined above.

More preferably the VLDL receptor portion of the fusion protein is able to cause specific removal of VLDL from the blood stream. Generally, such nucleic acid encoding the VLDL receptor will have homology to Sequence ID Nos. 1 or 2, corresponding to human and mouse VLDL receptor nucleic acid sequences, respectively (Sequence ID No. 3 sets forth the human VLDL receptor amino acid sequence encoded by Sequence ID No. 1; Sequence ID No. 4 sets forth the mouse VLDL receptor amino acid sequence encoded by Sequence ID No. 2). That is it will have at least about 70% sequence identity along the length of the nucleic acid, preferably at least 80%, 90% or even 100% identity for at least 100, 200 or all nucleotide bases. Such nucleic acid is thus distinct from that encoding an LDL receptor. In a preferred embodiment, the isolated nucleic acid sequence encodes a human or mouse VLDL receptor including additions, deletions or modifications to some or all of the sequence of the nucleic acid. That is, the nucleic acid sequences may be altered at its 5' end 3' end, or at any point intermediate the 5' or 3' ends of the sequence.

By "modification" is meant that nucleic acid base analogues as are known in the art may be present, or that one base, for example adenine may be substituted for another base, for example, guanine; the phosphodiester linkage may be modified as is known in the art, for example by substitution of a thioester linkage; or the sugar moiety of the nucleic acid may be modified as is known in the art, for example, substitution of 2'-deoxyribose with 2', 3'-ribose or substitution of 2', 3'-ribose with 2'-deoxyribose. These modifications may be made to one or more bases in the nucleic acid sequence. Modifications also include changes which, for example, stabilize the nucleic acid, but do not effect the function of the VLDL receptor (as can be determined by routine testing). Additionally, protein sequences comprising less than a whole VLDL receptor but which are nevertheless functional, may be mapped by mutational analysis or various clones may be created and the activity of proteins expressed from such clones assayed or other routine testing as is known in the art may be utilized.

In another preferred embodiment, the present invention includes a nucleic acid sequence, other than the sequence set forth as Sequence ID Nos. 1 or 2 but which will specifically hybridize to a segment of the nucleic acid sequence of the human or mouse VLDL receptor. This includes nucleic acid sequences which hybridize to any segment of the human or mouse VLDL receptor in a manner which is indicative of specific binding as opposed to non-specific background binding under conditions of stringency which would decrease non-specific binding, but would not be considered highly stringent. It does not include LDL receptor encoding nucleic acid sequences. In a preferred embodiment the invention includes a nucleic acid sequence other than the sequence set forth as Sequence ID Nos. 1 or 2 wherein the sequence will only hybridize to a segment of the nucleic acid sequence of the human or mouse VLDL receptor under highly stringent conditions. By "highly stringent conditions" is meant that non-specific hybridization would be expected to occur at a very low rate, e.g., hybridization would not be expected if there is more than about one nucleic acid base mismatch per 20 nucleotide bases of human or mouse VLDL receptor nucleic acid sequence.

In another preferred embodiment, a nucleic acid sequence encoding a VLDL receptor is provided within a vector. The term "vector" as used herein refers to a nucleic acid, e.g., DNA derived from a plasmid, cosmid, phagemid or bacteriophage, into which fragments of nucleic acid may be inserted or cloned. The vector can contain one or more unique restriction sites for this purpose, and may be capable of autonomous replication in a defined host or organism such that the cloned sequence is reproduced. The vector molecule can confer some well-defined phenotype on the host organism which is either selectable or readily detected. Some components of a vector may be a DNA molecule further incorporating a DNA sequence encoding a therapeutic or desired product, and regulatory elements for transcription, translation, RNA stability and replication. A viral vector in this sense is one that contains a portion of a viral genome, e.g., a packaging signal, and is not merely DNA or a located gene within a viral article. The term "VLDL receptor vector" is synonymous with the above-recited definition.

In a preferred embodiment, a vector comprising nucleic acid encodes a VLDL receptor, wherein the VLDL receptor vector is adapted to cause expression of a VLDL receptor. Expression includes the efficient transcription of an inserted gene or nucleic acid sequence within the vector. Expression products may be proteins, polypeptides or RNA. By "expression of a VLDL receptor" is meant that a complete or functional partial VLDL receptor protein is produced from the vector containing the nucleic acid encoding a VLDL receptor.

In another preferred embodiment, a vector having nucleic acid sequences encoding a VLDL receptor is provided in which the nucleic acid sequence is expressed only in specific tissue. That is, a complete or partial functional VLDL receptor is produced from the vector containing the nucleic acid encoding a VLDL receptor only in one or more predetermined, desired tissues. For example, muscle only, or liver only, or muscle and liver only.

In a preferred embodiment, a vector for the expression of a VLDL receptor nucleic acid sequence has a tissue-specific promoter, a VLDL receptor encoding nucleic acid sequence, and a post-transcriptional processing control sequence. The term "tissue-specific promoter" means that the promoter will allow transcription of RNA from the vector primarily only in a specific tissue in which the promoter is activated. For example, muscle cell specific promoters will only allow transcription in muscle cells. However, even with tissue-specific promoters some low level (about 10% or less than that observed in the desired tissue) expression might occur in other cell types. The promoter would still be defined as tissue specific. Methods of achieving tissue-specific gene expression as set forth in International Publication No. WO 93/09236, filed Nov. 3, 1992 and published May 13, 1993; International Application No. PCT/US93/03993, filed Apr.

28, 1993; International Application No. PCT/US93/03985, filed Apr. 28, 1993; and U.S. patent application entitled "Specific Expression Vectors and Methods of Use", filed Nov. 1, 1993 and U.S. Pat. application entitled "Keratin K1 Expression Vectors and Methods of Use"; all (including drawings) hereby incorporated by reference herein. By "post-transcriptional processing control sequence" is meant, for example, sequences which control intron deletion and exon splicing, polyadenylation or other modifications affecting RNA stability or RNA transport to cellular locations.

In all of the preceding vectors set forth above, a further aspect of the invention is that the nucleic acid sequence contained in the vector may include additions, deletions or modifications to some or all of the sequence of the nucleic acid, as defined above.

Yet an additional preferred embodiment, comprises a cell stably transfected with a VLDL receptor vector. The term "transfected" as used herein refers to a cell having undergone the process of introduction of nucleic acid or a nucleic acid vector into a cell. Various methods of transfecting a cell are possible including microinjection, CaPO$_4$ precipitation, lipofection (liposome fusion), electroporation and use of a gene gun. The term "stable" as used herein refers to the introduction of a gene into the chromosome of the targeted cell where it integrates and becomes a permanent component of the genetic material in that cell. An episomal transfection is a variant of stable transfection in which the introduced gene is not incorporated in the host cell chromosomes but rather is replicated as an extrachromosomal element. This can lead to apparently stable transfection of the characteristics of a cell.

A cell may be co-transfected with a vector containing a selectable marker. This selectable marker is used to select those cells which have become transfected. Types of selectable markers which may be used are well known to those of ordinary skill in the art.

In another preferred embodiment, there is provided a transfected cell wherein the VLDL receptor is expressed as a cell surface protein. By "cell surface protein" is meant a protein which wholly or partially spans the cell membrane, and which is exposed on the surface of the cell.

In still another preferred embodiment, there is provided a transfected cell wherein a VLDL receptor is expressed as a secreted protein. By "secreted protein" is meant a protein which is not associated with the cell membrane, but rather is intracellularly processed for secretion into the extracellular environment or other cellular compartment.

Alternatively, a transfected cell containing a VLDL receptor vector may only be transiently transfected, resulting in transient expression of a VLDL receptor. The term "transient" as used herein relates to the introduction of a gene into a cell to express a VLDL receptor, where the introduced gene is not integrated into the host cell genome and is accordingly eliminated from the cell over a period of time. Transient expression relates to the expression of a gene product during a period of transient transfection.

In yet a further preferred embodiment, there is provided a cell stably transformed with a VLDL receptor vector. The term "transformed" as used herein refers to a process or mechanism of inducing transient or permanent changes in the characteristics (expressed phenotype) of a cell by the mechanism of gene transfer whereby DNA or RNA is introduced into a cell in a form where it expresses a specific gene product or alters the expression or effect of endogenous gene products. The term "stable" as used herein refers to the introduction of gene(s) into the chromosome of the targeted cell where it integrates and becomes a permanent component of the genetic material in that cell. Gene expression after stable transformation can permanently alter the characteristics of the cell leading to stable transformation. An episomal transformation is a variant of stable transformation in which the introduced gene is not incorporated in the host cell chromosomes but rather is replicated as an extrachromosomal element. This can lead to apparently stable transformation of the characteristics of a cell.

Cells may be co-transformed with a vector containing a selectable marker. This selectable marker is used to select those cells which have become transformed. Types of selectable markers which may be used are well known to those of ordinary skill in the art.

The embodiments and definitions set forth above with respect to transfected cells, relating to cell surface proteins and secreted proteins, are equally applicable to VLDL receptor expressed in stably transformed cells.

A cell transformed with a VLDL receptor vector may only be transiently transformed, resulting in transient expression of VLDL receptors. The term "transient" as used in transiently transformed is identical to that set forth with respect to transfected cells.

An additional preferred embodiment, provides for a transgenic animal containing a VLDL receptor vector. By "transgenic animal" is meant an animal whose genome contains an additional copy or copies of the gene from the same species or it contains the gene or genes of another species, such as a gene encoding a VLDL receptor introduced by genetic manipulation or cloning techniques, as described herein and as known in the art. The transgenic animal can include the resulting animal in which the vector has been inserted into the embryo from which the animal developed or any progeny of that animal. The term "progeny" as used herein includes direct progeny of the transgenic animal as well as any progeny of succeeding progeny. Thus, one skilled in the art will readily recognize that if two different transgenic animals have been made each utilizing a different gene or genes and they are mated, the possibility exists that some of the resulting progeny will contain two or more introduced genes. One skilled in the art will readily recognize that by controlling the matings, transgenic animals containing multiple introduced genes can be made.

A further preferred embodiment comprises a ligand capable of specifically binding to a VLDL receptor wherein the ligand has associated with it a detectable label. A "ligand" is a molecule or an assemblage of molecules capable of specifically binding to a VLDL receptor. The term "specifically binding" means that a labelled ligand bound to a VLDL receptor can be competeably displaced from the VLDL receptor by the addition of unlabelled ligand, as is known in the art. An example of a ligand would be a monoclonal antibody specific for the VLDL receptor. The term "associated with" means that the ligand is either covalently or ionically or hydrophobically or otherwise linked to the detectable label, such that wherever the detectable label is found the ligand will also be found. A "detectable label" is a molecule, for example, an enzyme, a proenzyme, a fluorescent or bioluminescent or radioactive molecule which will give rise to a signal including but not limited to: Production of luminescent or fluorescent products, alteration of luminescence, chemiluminescence or its alteration, light absorbent products, pH changes, magnetic resonance imaging changes, alteration in the absorption or emission of electromagnetic radiation, gravimetric, volumetric, or electrochemical changes, or precipitation or agglutination.

In another preferred embodiment, a method of introducing a continuous supply of VLDL receptor into an animal or a tissue culture by administering an effective amount of a vector is provided. By "continuous" is meant that the VLDL receptor is constitutively expressed without the need for the addition of an exogenously administered activating compound to initiate expression. The term "effective amount" means an amount sufficient to give expression of some amount of VLDL receptor in the muscle or tissue culture. This amount may be as low as expression of about one VLDL receptor per thousand cells.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

In another preferred embodiment, there is provided a method of introducing into an animal a VLDL receptor vector containing a VLDL receptor of another species and capable of expressing in whole or in part or in modified form this other species VLDL receptor. This transgenic animal is useful in screening compounds for their pharmacological effects on lipoprotein metabolism comprising the steps of administering compounds to the transgenic animal and measuring lipoprotein metabolism in the transgenic animal. The term "administering" includes any of the methods of administration described below in the Detailed Description of the Invention section. The term "pharmacological effects" means that a compound increases or decreases the serum level of a particular lipoprotein by any mechanism, including, but not limited to, directly or indirectly decreasing lipoprotein synthesis, increasing lipoprotein uptake, excretion or conversion to another substance.

In another preferred embodiment, an in vivo method of administering a nucleic acid sequence is provided, as described below. In a further preferred embodiment, naked DNA may be administered. The term "naked DNA" means substantially pure DNA which is not associated with protein, lipid, carbohydrate or contained within a cell or an artificial delivery system such as a liposome. A tissue or cell may also be transduced with a VLDL receptor vector. The term "transduced or transduction" as used herein refers to the process of introducing a recombinant virus into a cell by infecting the cell with the virus particle. The virus may be administered substantially simultaneously, i.e., the VLDL nucleic acid sequence and the virus may administered in the same composition or that the administration of one may follow the other by about up to one hour.

In an additional preferred embodiment a method of administering VLDL nucleic acid sequence through cell surface receptor mediated endocytosis is provided. That is, the biological process whereby cell surface receptors which have bound a ligand cluster together on the cell surface followed by invagination of the cell membrane containing the clustered receptors and formation of an intercellular vesicle containing the receptor ligand complexes. A "cell surface receptor" is a specific chemical grouping on the surface of a cell to which a ligand can attach. Cell surface receptors which may be used in the present invention include the folate receptor, the biotin receptor, the lipoic acid receptor, the low density lipoprotein receptor, the asialoglycoprotein receptor, IgG antigenic sites, insulin-like growth factor type II/cation-independent mannose-6-phosphate receptor, calcitonin gene-related peptide receptor, insulin-like growth factor I receptor, nicotinic acetylcholine receptor, hepatocyte growth factor receptor, endothelin receptor, bile acid receptor. Further, incorporating DNA into macromolecular complexes that undergo endocytosis increases the range of cell types that will take up foreign genes from the extracellular space. Such complexes may include lipids, polylysine, viral particles, ligands for specific cell-surface receptors or nuclear proteins.

The term "DNA transporter" refers to a molecular complex which is capable of non-covalently binding to DNA and efficiently transporting the DNA through the cell membrane. Although not necessary, it is preferable that the transporter also transport the DNA through the nuclear membrane. The methods and material set forth in International Publication No. WO 93/18759, filed Mar. 19, 1993 and published Sep. 30, 1993 are hereby incorporated by reference.

In another preferred embodiment, a two-component system of administering a VLDL nucleic acid sequence is provided. The term "two-component system" means a system utilizing a packaging cell which produces a viral vector. In a preferred embodiment, a partial hepatectomy may be performed prior to administration of the packaging cell.

The term "hepatectomy" or "partial hepatectomy" is used as is commonly understood in the art.

In an additional preferred embodiment, a retroviral vector containing a modified retroviral envelope glycoprotein is provided. The term retroviral envelope glycoprotein is used as is commonly understood in the art.

In another preferred embodiment, a method of isolating additional animal lipoprotein receptor genes utilizing a probe or probes is provided. That is, genes with a nucleic acid sequence other than Sequence ID Nos. 1 or 2, which when expressed produce a functional lipoprotein receptor. Functional lipoprotein receptor is defined as above for the VLDL receptor, or is a receptor which will specifically bind a lipoprotein. The term "probe or probes" is used as is commonly understood in the art.

Another preferred embodiment provides for a method of enhancing the effect of administering a nucleic acid expression vector encoding a VLDL expression vector by also administering a nucleic acid expression vector encoding a lipoprotein lipase. The term "enhancing" means increasing the effect of administering a nucleic acid expression vector encoding a VLDL expression vector, whereby the amount of increased effect may be as small a difference as may be detected, utilizing methods known in the art. The term "lipoprotein lipase" is used as is commonly understood in the art. The term "administered substantially simultaneously" means that the nucleic acid expression vector encoding a VLDL receptor nucleic acid sequence and the expression vector encoding a lipoprotein lipase nucleic acid sequence may be administered in the same composition, or that the administration of one may follow the other by about up to one hour. The term "administered after some period of time" means that the nucleic acid expression vector encoding a VLDL receptor nucleic acid sequence and the expression vector encoding a lipoprotein lipase nucleic acid sequence may administered such that one follows the other by more than one hour.

In another preferred embodiment, a method of diagnostic imaging is provided. The term "diagnostic imaging" means the ability to perceive the tissue distribution of a VLDL receptor in a particular animal in vivo or a in a tissue ex vivo. The term "unimageable compound" means a compound which generates a signal detectable as a human perceivable visual signal, an electromagnetic signal, a radioactive signal or a signal detectable by magnetic resonance imaging, positron emission tomography or computerized axial tomography as is known in the art.

Therapeutic agents, such as a VLDL receptor vector and VLDL receptor protein that lower plasma VLDL will accomplish two important objectives: first, they will lower IDL and LDL, the metabolic products of VLDL, and total plasma cholesterol, and second, they will simultaneously lower triglycerides. The lowering of IDL and LDL and total plasma cholesterol is highly desirable because of the known strong association between these lipid parameters and coronary heart disease. The lowering of triglyceride is also of benefit especially when it occurs in the presence of atherogenic dyslipidemias which is a common occurrence. Use of the VLDL receptor vector and VLDL receptor protein should also effectively lower LDL in homozygous FH patients because VLDL is the precursor of LDL. Furthermore, the VLDL receptor offers an important advantage over the LDL receptor. FH patients have either no LDL receptor or abnormal LDL receptor. With the expression of the normal LDL receptor, they will develop antibodies to the protein which will eventually interfere with the continued expression of the LDL receptor and the effectiveness of treatment. The VLDL receptor, on the other hand, is normally present in multiple tissues in these patients. Therefore, the induced overexpression of the VLDL receptor in tissues that normally produce it, or the induced expression of the receptor in an ectopic site such as the liver will not cause any untoward immunological response. This is a major advantage of the use of the VLDL receptor. Use of the VLDL receptor vector and VLDL receptor protein will decrease or eliminate the need for invasive surgical procedures, such as heart bypass surgery or balloon angioplasty.

Other and further objects, features and advantages will be apparent from the following description of the presently preferred embodiments in the invention.

DETAILED DESCRIPTION OF THE INVENTION

The drawings will first briefly be described.
Drawings

FIG. 1 illustrates the nucleic acid sequence of a human VLDL receptor (SEQ ID NO: 1).

FIG. 2 illustrates the nucleic acid sequence of a mouse VLDL receptor (SEQ ID NO: 2).

FIG. 3 illustrates the amino acid sequence of a human VLDL receptor encoded by Sequence ID No. 1, utilizing the one letter code as is well known in the art (SEQ ID NO: 3).

FIG. 4 illustrates the amino acid sequence of a mouse VLDL receptor encoded by Sequence ID No. 2, utilizing the one letter code as is well known in the art (SEQ ID NO: 4).

VLDL RECEPTOR

The amino acid sequences of the human and mouse VLDL receptors have been deduced from their respective cloned cDNAs which were isolated and sequenced. See, Sequence ID Nos. 1 and 2. Each protein is predicted to contain 873 amino acid residues, including 27 residues in the signal peptide. Thus, the two proteins are identical in size. The cDNA nucleotide sequences and predicted amino acid sequences also show high homology between the two species. (The cDNA for the rabbit VLDL receptor has been cloned. Takahashi et al., Proc. Natl. Acad. Sci. U.S.A., 89: 9252–9256, (1992)).

The N-terminal 27 amino acid sequence (residues −27 to −1) is hydrophobic in nature and constitutes the putative signal peptide. The mature human and mouse VLDL receptor protein contains three potential N-linked glycosylation sites (Asn-124, 737 and 754). Like the LDL receptor (Yamamoto et al., Cell 39: 27–38, 1984; Yamamoto et al., Science 232: 1230–1237, 1986), the human and mouse VLDL receptor can be divided into five domains. At the N-terminal region are 8-fold ~40 residue cysteine-rich repeats that are homologous to the ligand binding region of the LDL receptor which contains 7-fold repeat units (Esser et al., J. Biol. Chem. 263: 13282–13290, 1988; Russell et al., J. Biol. Chem. 264: 21682–21688, 1989). The next domain, which has homology to the epidermal growth factor precursor, spans 396 amino acids including three cysteine-rich repeats, designated A, B and C. This domain in the LDL receptor is thought to be important for the acid-dependent dissociation of the ligand from the receptor (Davis et al., Nature 326: 760–765, 1987). The next domain, the clustered O-linked sugar region, is well conserved among the known mammalian VLDL receptor sequences. The last two domains, the transmembrane domain and the cytoplasmic domain, are completely conserved with no amino acid change between human and mouse VLDL receptors. In the LDL receptor, there is a conserved tetrapeptide NPXY (Asn-Pro-X-Tyr) (wherein X is any amino acid) in the cytoplasmic domain which is required for clustering of the LDL receptor in coated pits (Chen et al., J. Biol. Chem. 265: 3116–3123, 1990). In the human, mouse and rabbit VLDL receptor, the tetrapeptide has the sequence NPVY (Asn-Pro-Val-Tyr). Overall, the VLDL receptor has evolved at a much slower rate than the LDL receptor.

The cloned human VLDL receptor cDNA probe was used to localize the VLDL receptor gene on chromosomal spreads by fluorescence in Situ hybridization. A hybridization signal was consistently observed on chromosome band 9p24. Thus, the VLDL receptor is on a chromosome different from the LDL receptor which is located on chromosome 19p13 (Lindgren et al., Proc. Natl. Acad. Sci. U.S.A. 82: 8567–8571, 1985).

The VLDL receptor binds to apolipoprotein (apo) E-containing lipoproteins, including VLDL, intermediate density lipoprotein (IDL), and β-VLDL. It may also bind to chylomicrons and chylomicron remnants which also contain apoE. Unlike an LDL receptor, a VLDL receptor will not competeably bind to and internalize LDL. As described above, a VLDL receptor encompasses any fragment of a VLDL receptor which exhibits functional properties of a VLDL receptor as defined above.

VLDL are the precursors of IDL and LDL. Both IDL and LDL have been identified as important risk factors for atherosclerosis. Therefore, any therapeutic intervention that lowers IDL and LDL will reduce their atherogenic potential. There is recent evidence that lowering serum cholesterol and LDL may actually cause regression of atheromatous lesions. Elevated triglycerides are positively correlated with risk for coronary heart disease. Much of this association may be related to the fact that high triglycerides often occur in the presence of reduced high density lipoproteins (HDL). HDL is thought to be anti-atherogenic and low HDL predisposes one to atherosclerosis. Furthermore, high triglycerides are often associated with atherogenic forms of LDL (e.g., in familial combined hyperlipidemia and diabetic dyslipidemia).

Therapeutic agents that lower plasma VLDL will accomplish two important objectives: first, they will lower IDL and LDL, the metabolic products of VLDL, and total plasma cholesterol, and second, they will also lower triglyceride levels. The lowering of IDL and LDL and total plasma cholesterol is highly desirable because of the known strong association between these lipid parameters and coronary heart disease. The lowering of triglyceride is also of benefit especially when it occurs in the presence of atherogenic dyslipidemias, a common situation. In fact, therapeutic intervention in this situation is recommended by the National Cholesterol Education Program (NCEP) Expert Panel (Adult Treatment Panel II) (JAMA 269: 3015–3023, 1993).

It would be useful to control blood levels of β-VLDL VLDL and IDL through the use of exogenously administered VLDL receptor binding to these ligands, thereby decreasing the risk of cardiovascular disease and the resulting need for invasive surgical procedures directed at the heart.

Currently, there is a clinical protocol approved for the treatment of LDL receptor deficient homozygous FH patients by somatic gene therapy using the human LDL receptor gene (Wilson, Hum. Gene Ther. 3: 179–222, 1992). Use of the VLDL receptor should also effectively lower LDL in homozygous FH patients because VLDL is the precursor of LDL. Furthermore, the VLDL receptor offers one important advantage over the LDL receptor. FH patients have either no LDL receptor or abnormal LDL receptor. With the expression of the normal LDL receptor, they will develop antibodies to the protein which will eventually interfere with the continued expression of the LDL receptor and the effectiveness of treatment. The VLDL receptor, on the other hand, is normally present in multiple tissues in these patients. Therefore, the induced over-expression of the VLDL receptor in tissues that normally produce it, or the induced expression of the receptor in an ectopic site such as the liver will not cause any untoward immunological response. This is a major advantage of the use of the VLDL receptor.

Administration

The nucleic acid sequence encoding VLDL receptor can be administered prophylactically, or to patients having a disease or condition characterized by an elevated plasma lipoprotein level, e.g., by exogenous delivery of the nucleic acid sequence encoding VLDL receptor as naked DNA, DNA associated with specific carriers, or in a nucleic acid expression vector to a desired tissue by means of an appropriate delivery vehicle, e.g., a liposome, by use of iontophoresis, electroporation and other pharmacologically approved methods of delivery. Routes of administration may include intramuscular, intravenous, aerosol, oral (tablet or pill form), topical, systemic, ocular, as a suppository, intraperitoneal and/or intrathecal.

The specific delivery route of a VLDL receptor will depend on the use of the VLDL receptor.

Some methods of delivery that may be used include:
a. encapsulation in liposomes,
b. transduction by retroviral vectors,
c. localization to nuclear compartment utilizing nuclear targeting site found on most nuclear proteins,
d. transfection of cells ex vivo with subsequent reimplantation or administration of the transfected cells,
e. a DNA transporter system.

At least three types of delivery strategies are useful in the present invention, including: Injection of naked VLDL receptor DNA or charge modified naked VLDL receptor DNA, particle carrier drug delivery vehicles which are also suitable for delivery of VLDL receptor proteins, and retroviral expression vectors. Unmodified nucleic acid sequence encoding VLDL receptors, like most small molecules, are taken up by cells, albeit slowly. To enhance cellular uptake, the nucleic acid sequence encoding VLDL receptor may be modified in ways which reduce its charge but will maintain the expression of specific functional groups in the final translation product. This results in a molecule which is able to diffuse across the cell membrane, thus removing the permeability barrier.

Chemical modifications of the phosphate backbone will reduce the negative charge allowing free diffusion across the membrane. This principle has been successfully demonstrated for antisense DNA technology which shows that this is a feasible approach. In the body, maintenance of an external concentration will be necessary to drive the diffusion of the modified nucleic acid sequence encoding the VLDL receptor into the cells of the tissue. Administration routes which allow the tissue to be exposed to a transient high concentration of the nucleic acid sequence encoding the VLDL receptor, which is slowly dissipated by systemic adsorption are preferred. Intravenous administration with a drug carrier designed to increase the circulation half-life of the nucleic acid sequence encoding the VLDL receptor or VLDL receptor proteins can be used. The size and composition of the drug carrier restricts rapid clearance from the blood stream. The carrier, made to accumulate at the desired site of transfer, can protect the nucleic acid sequence encoding the VLDL receptor from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels may be potential delivery vehicles for a nucleic acid sequence encoding a VLDL receptor. These carriers have been developed for chemotherapeutic agents and protein-based pharmaceuticals (such as VLDL receptor proteins), and consequently, can be adapted for nucleic acid delivery.

Chemical modification of the nucleic acid sequence encoding a VLDL receptor to neutralize negative charge may be all that is required for penetration. However, in the event that charge neutralization is insufficient, the nucleic acid sequence encoding a VLDL receptor can be co-formulated with permeability enhancers, such as Azone or oleic acid, in a liposome. The liposomes can either represent a slow release presentation vehicle in which the modified nucleic acid sequence encoding a VLDL receptor and permeability enhancer transfer from the liposome into the targeted cell, or the liposome phospholipids can participate directly with the modified nucleic acid sequence encoding a VLDL receptor and permeability enhancer can participate directly with the modified nucleic acid encoding a VLDL receptor and permeability enhancer facilitating cellular delivery. In some cases, both the nucleic acid encoding a VLDL receptor and permeability enhancer can be formulated into a suppository formulation for slow release.

The nucleic acid sequence encoding a VLDL receptor or a VLDL receptor protein may also be systemically administered. Systemic absorption refers to the accumulation of drugs in the blood stream followed by distribution throughout the entire body. Administration routes which lead to systemic absorption include: intravenous, intramuscular, subcutaneous, intraperitoneal, intranasal, intrathecal and ophthalmic. A gene gun may also be utilized. Administration of DNA-coated microprojectiles by a gene gun requires instrumentation but is as simple as direct injection of DNA. A construct bearing the gene of interest is precipitated onto the surface of microscopic metal beads. The microprojectiles are accelerated with a shock wave or expanding helium gas, and penetrate tissues to a depth of several cell layers. This approach permits the delivery of foreign genes to the skin of anesthetized animals. This method of administration achieves expression of transgenes at high levels for several days and at detectable levels for several weeks. Each of these administration routes exposes the nucleic acid sequence encoding a VLDL receptor to an accessible targeted tissue. Subcutaneous administration drains into a localized lymph node which proceeds through the lymphatic network into the circulation. The rate of entry into the circulation has been shown to be a function of molecular weight or size. The use of a liposome or other drug carrier localizes the nucleic acid sequence encoding VLDL receptor at the lymph node. The nucleic acid sequence encoding VLDL receptor can be modified to diffuse into the cell, or the liposome can directly participate in the delivery of either the unmodified or modified nucleic acid sequence encoding VLDL receptor to the cell.

Liposomes injected intravenously show accumulation in the liver, lung and spleen. The composition and size can be adjusted so that this accumulation represents 30% to 40% of the injected dose. The remaining dose circulates in the blood stream for up to 24 hours.

The chosen method of delivery should result in cytoplasmic accumulation and molecules should have some nuclease-resistance for optimal dosing. Nuclear delivery may also be used. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 1–1000 µg/kg of body weight/day. The duration of treatment will extend through the course of the disease symptoms, possibly continuously. The number of doses will depend upon disease delivery vehicle and efficacy data from clinical trials.

Another method of administration involves the use of a DNA transporter system for inserting specific DNA into a cell. The DNA transporter system comprises a plurality of a first DNA binding complex, said complex including a first binding molecule capable of non-covality binding to DNA, said first binding molecule covalently linked to a surface ligand, said surface ligand capable of binding to a cell surface receptor; a plurality of a second DNA binding complex, said complex including a second binding molecule capable of non-covalently binding to DNA, said second binding molecule covalently linked to a nuclear ligand, said nuclear ligand capable of recognizing and transporting a transporter system through a nuclear membrane; wherein said plurality of first and second DNA binding complexes are capable of simultaneously, non-covalently binding to a specific DNA.

Additionally, a plurality of a third DNA binding complex may be used, said complex includes a third binding molecule capable of non-covalently binding to DNA, said third binding molecule covalently linked to a virus; wherein said plurality of third DNA binding complexes are capable of simultaneously, non-covalently binding to a specific DNA.

The first binding molecule, the second binding molecule and third binding molecule can each be selected from the group consisting of spermine, spermine derivative, histones, cationic peptides and polylysine. Spermine derivative refers to analogues and derivatives of spermine and include compounds as set forth in International Publication No. WO 93/18759, filed Mar. 19, 1993 and published Sep. 30, 1993 hereby incorporated by reference.

Establishment of therapeutic levels of nucleic acid sequence encoding VLDL receptor within the cell is dependent upon the rates of uptake and degradation. Decreasing the degree of degradation will prolong the intracellular half-life of the VLDL receptor gene. Descriptions of useful systems are provided in the art cited above, all of which is hereby incorporated by reference.

A VLDL receptor nucleic acid sequence may be administered utilizing an ex vivo approach whereby cells are removed from an animal, transduced with the VLDL receptor nucleic acid sequence and reimplanted into the animal. The liver can be accessed by an ex vivo approach by removing hepatocytes from an animal, transducing the hepatocytes in vitro with the VLDL receptor nucleic acid sequence and reimplanting them into the animal (e.g., as described for rabbits by Chowdhury et al, Science 254: 1802–1805, 1991, or in humans by Wilson, Hum. Gene Ther. 3: 179–222, 1992) incorporated herein by reference.

The VLDL receptor nucleic acid sequence may be administered utilizing an in vivo approach whereby the gene will be administered directly to an animal by intravenous injection, intramuscular injection, or by catheterization and direct delivery of the gene via the blood vessels supplying the target organ. Since the VLDL receptor is normally expressed in multiple tissues and organs including heart, skeletal muscle, adipose tissues, spleen, lung, brain, kidney, testis, adrenal, small intestine, and other tissues, any of these tissues can be target organs. Among these tissues, skeletal muscle is one tissue that is readily accessible by intramuscular injection or intravenous injection. Expression will be achieved using a skeletal muscle-specific promoter for the nucleic acid sequence encoding VLDL receptor.

Normally there is little expression of the VLDL receptor in the liver. This organ is, however, also a good target organ for expression because the liver clears large volumes of blood and is able to metabolize the apoE-containing lipoproteins that bind to the VLDL receptor and become internalized in this organ. The liver can also be accessed by an in vivo approach by administration of the nucleic acid sequence encoding VLDL receptor intravenously, intraportally (via the portal vein) or intra-arterially into the hepatic artery.

Many nonviral techniques for the delivery of a VLDL receptor nucleic acid sequence into a cell can be used, including direct naked DNA uptake (e.g., Wolff et al., Science 247: 1465–1468, 1990), receptor-mediated DNA uptake, e.g., using DNA coupled to asialoorosomucoid which is taken up by the asialoglycoprotein receptor in the liver (Wu and Wu, J. Biol. Chem. 262: 4429–4432, 1987; Wu et al., J. Biol. Chem. 266: 14338–14342, 1991), and liposome-mediated delivery (e.g., Kaneda et al., Expt. Cell Res. 173: 56–69, 1987; Kaneda et al., Science 243: 375–378, 1989; Zhu et al., Science 261: 209–211, 1993). Many of these physical methods can be combined with one another and with viral techniques; enhancement of receptor-mediated DNA uptake can be effected, for example, by combining its use with adenovirus (Curiel et al., Proc. Natl. Acad. Sci. U.S.A. 88: 8850–8854, 1991; Cristiano et al., Proc. Natl. Acad. Sci. U.S.A. 90: 2122–2126, 1993).

Vectors

The construction of expression vectors encoding a VLDL nucleic acid sequence encoding a VLDL receptor in whole or in part or in modified form will be performed utilizing standard techniques known to those of ordinary skill in the art as set forth in, for example, Maniatis, Fritsch and Sambrook, Molecular Cloning: A Laboratory Manual. Cold Spring Harbor Laboratory, Cold Spring Harbor, N.Y. 1982. The nucleic acid sequence encoding a VLDL receptor or a functional part thereof will be inserted at one end of a promoter, typically but not necessarily the 3' end, the promoter capable of directing appropriate transcription of the VLDL nucleic acid sequence. The promoter used can be any that gives good expression of a VLDL receptor, these include the retroviral long terminal repeat (LTR) promoter, RSV-LTR, MuV-LTR, promoters from cytomegalovirus, apolipoprotein A-I, albumin (together with its enhancer), transthyretin, transferrin, skeletal muscle actin, metallothionein, or a myogenic specific promoter selected from a group consisting of skeletal alpha actin gene promoter, first myosin light chain 1 promoter, myosin heavy chain promoter, tropinin T promoter, muscle creatinine kinase promoter/enhancer, cytomegalovirus promoter, RSV promoter and Rous Sarcoma virus LTR. In the preferred embodiment the skeletal alpha actin promoter is used. Other promoters as are known in the art may also be used. Also, specific embodiments may include the addition of regulatory promoter elements to regulate the expression of any specific nucleic acid sequence in myogenic tissue. In the preferred embodiment, Vitamin D is used to regulate expression. One skilled in the art will recognize that the selection of the promoter will depend on the vector, the VLDL receptor nucleic acid sequence utilized and the desired biological effect. One skilled in the art will also recognize that in the selection of a promoter the parameters can include: achieving sufficiently high levels of gene expression to achieve a physiological effect; maintaining a critical steady state of gene expression; achieving temporal regulation of gene expression; achieving tissue-specific expression; achieving pharmacological, endocrine, paracrine or autocrine regulation of gene expression; and preventing inappropriate or undesirable levels of expression. Any given set of selection requirements will depend on the conditions, but can be readily determined once the specific requirements are determined.

Genomic sequences comprising an intron or introns and in certain embodiments including regulatory sequences for transcription or RNA stability may be included. These may include 3' untranslated sequences possibly including regulatory sequences for RNA stability. A polyadenylation signal from genes such as growth hormone or SV40 or others as are known in the art will be ligated to one end of the nucleic acid sequence, typically the 3' end of the nucleic acid sequence.

In the case of a retroviral vector the elements include two long terminal repeat sequences, the Y (packaging) sequence which may extend into the gag region of the retrovirus and may be modified to eliminate splice signals or translation initiation sites, a promotor capable of producing appropriately regulated transcription of VLDL receptor nucleic acid sequences. In alternate embodiments the retroviral vector can include a selectable marker for chemical, pharmacological, or fluorescent elimination of non-transduced cells and/or other retroviral sequences required for integrity and function of the retroviral vector.

A number of viral vectors can be used to deliver a VLDL receptor nucleic acid sequence, including papovaviruses, adenovirus, vaccinia virus, adeno-associated virus, herpesviruses, retroviruses of avian, murine, and human origin and other viruses as are known in the art (reviewed by Morgan and Anderson, Ann. Rev. Biochem. 62: 191–217, 1993 incorporated herein by reference.) Retroviral vectors can be used for transducing the VLDL receptor vector into liver cells or muscle. The advantage of retrovirus as a delivery system is the ability of the virus to integrate into the host cell chromosomes (reviewed by A. D. Miller, Hum. Gene Ther. 1: 5–14, 1990). The VLDL receptor vector can be delivered by retroviral-mediated gene transfer, a two-component system consisting of the packaging cell and the viral vector. The VLDL receptor nucleic acid sequence can be inserted into the retroviral vector by molecular cloning (e.g., as described by Wilson, Hum. Gene Ther. 3: 179–222, 1992). The virus particle assembled by the producer cell line (i.e., a packaging cell line containing the VLDL receptor-containing retroviral vector) will be used to transfer the VLDL receptor nucleic acid sequence to a target organ or tissue such as liver cells in vivo (following partial hepatectomy because only dividing cells take up retroviral vectors), isolated hepatocytes in vitro or skeletal muscle in vivo. The virus particle will bind to the cell and deliver the VLDL receptor nucleic acid sequence which is integrated into the host genome and result in stable long-term expression of the VLDL receptor.

Two major limitations to the use of retroviral vectors are the restricted host-cell range and the inability to obtain high-titer virus. These limitations have been overcome by Burns et al., Proc. Natl. Acad. Sci. U.S.A. 90: 8033–8037, 1993. They replaced the retroviral envelope glycoprotein with the G glycoprotein of vesicular stomatitis virus. Such vectors can be produced in high titer (>$10^9$ colony-forming units/ml) and can infect diverse cell types. Partial hepatectomy may not be necessary for liver expression using such vectors. The nucleic acid sequence encoding VLDL receptor can be delivered by using this or a similarly designed vector in vivo by intravenous administration.

The other viral vector delivery system that will be used is the adenovirus system. The VLDL receptor nucleic acid sequence can be used to replace the E1 region of the adenovirus using the method described by Graham and Prevec (Methods Molec. Biol., Vol. 7, E. J. Murray, ed., Humana Press, New Jersey, pp. 109–128, 1991) using recombination in 293 cells incorporated herein by reference. The replication-defective VLDL receptor nucleic acid sequence/adenovirus can be injected intravenously, intramuscularly, intraportally or intra-arterially (hepatic artery). To date, adenovirus-mediated expression vectors generally direct the transient expression of the therapeutic gene. Improvements and refinements in vector structure and design may lead to diminished immunogenicity and allow the vector to be administered repeatedly. Other modifications may result in the ability of the VLDL receptor nucleic acid sequence to be integrated in the host chromosomes allowing for stable expression.

Other viral vector delivery systems as are known in the art will also be used for the targeted transfer of the VLDL receptor nucleic acid sequence.

The following examples are offered by way of illustration and are not intended to limit the invention in any manner.

EXAMPLE 1

Methods of Augmenting Levels of Expression of Human or Mouse VLDL Receptor Vector Normally, the VLDL receptor is expressed at a high level in skeletal muscle, although the exact level of expression has not been defined. For a therapeutic effect using muscle expression, it will be necessary to increase VLDL expression by about 5% or more. The persistent over-expression of the VLDL receptor in muscle by this amount should lead to a substantial lowering of plasma VLDL, IDL and LDL.

Liver normally does not express detectable amounts of VLDL receptor. Therefore, the induced expression of low level of VLDL receptor should have a substantial effect on plasma lipoproteins. The minimal level aimed at is an average expression of one molecule per cell (i.e., 1000 receptors per cell if 0.1% of hepatocytes show expression, 100 receptors per cell if 1% express it and so on). For patients with more severe elevation of LDL cholesterol, e.g., levels of about 200 mg/dL to 250 mg/dL or higher, a higher level of expression will be targeted, e.g., aiming at 10–1000 molecules per cell. The relatively high level of expression will be a function of the nucleic acid sequence encoding VLDL receptor construct (e.g., different promoters will have different activities) and the delivery method (e.g., naked DNA delivery, liposome delivery, receptor-mediated delivery, retrovirus-mediated delivery and adenovirus-mediated delivery will have different efficiencies, and in vivo versus ex vivo delivery will also produce different results) which can be experimented on and optimized. The level of expression will be determined at the RNA level by RNA blotting or S1 protection assay, and at the protein level by immunoblot analysis and by receptor-binding assay by the method of Goldstein et al., Methods Enzymol. 98: 241–260, 1983.

EXAMPLE 2

Methods of Enhancing VLDL Receptor Activity by Expression of Lipoorotein Lipase (LPL)

VLDL receptor and LPL are expressed in similar tissues, e.g., heart, skeletal muscle and adipose tissue. LPL has been found to play an important role in the receptor-mediated uptake of various lipoproteins (Eisenberg et al., J. Clin. Invest. 90: 2013–2021) via LDL receptor related protein ("LRP") (Chappell et al., J. Biol. Chem. 267: 25764–25767, 1992; Beisiegel et al., Proc. Natl. Acad. Sci. U.S.A. 88: 8342–8346, 1991), and LDL receptor (Mulder et al., J. Biol. Chem. 268: 9369–9375, 1993). It also may be involved in the non-receptor mediated uptake of lipoproteins (Mulder et al., J. Biol. Chem. 268: 9369–9375, 1993; Rumsey et al., J. Clin. Invest. 90: 1504–1512, 1992; Williams et al., J. Biol. Chem. 267: 13284–13292, 1992). The co-expression of LPL in the same tissues that express the VLDL receptor will enhance the activity of the latter. To accomplish this, an LPL gene vector will be delivered using a similar design as the VLDL gene vector. The two vectors can be delivered simultaneously, or they can be delivered consecutively with a varying period in between. It is expected that the activity of the VLDL receptor will be markedly enhanced by this method of co-expression.

EXAMPLE 3

Human or Mouse VLDL Receptor Variants

The human or mouse VLDL receptor may be used without modification for gene therapy. However, variants of the human or mouse nucleic acid sequence encoding VLDL receptor generated by site-specific mutagenesis and having the following properties, such as; increased affinity for the ligand, recognition of apoB-containing lipoproteins in addition to apoE-containing lipoproteins, or usefulness for screening for pharmaceutical agents that bind to the VLDL receptor and modulate its activity (see, Example 5 below) will also be useful. Selection from a wide variety of methods for site-directed mutagenesis for modifying the VLDL receptor, including the methods of Taylor et al., Nucleic Acids Res. 13: 8765–8785, 1985, and of Deng and Nickoloff, Anal. Biochem. 200: 81–88, 1992, incorporated herein by reference, may be used.

EXAMPLE 4

Determination of Serum Chemistry Values for Patients Undergoing VLDL Gene Therapy A large number of serum chemistry values will be obtained as for all patients with hyperlipidemia who are at risk for accelerated atherosclerosis. The following values are specifically measured with respect to VLDL receptor gene therapy: total serum cholesterol, triglyceride, LDL-cholesterol, HDL, apoA-I, apoE (level and isoform), apoB, and lipoprotein (a). The aim of VLDL gene therapy is to reduce total serum cholesterol (and triglyceride if it is elevated), LDL-cholesterol and both apoE and apoB. The effect of treatment on HDL and its major apolipoprotein, apoA-I, will be monitored. Lipoprotein (a) level is relatively resistant to various forms of medication. Since VLDL receptor gene therapy will lower the apoB-containing lipoproteins (VLDL, IDL and LDL), it is likely that the level of lipoprotein (a), which contains apoB-100 as an essential component, will also be lowered.

EXAMPLE 5

Screening for Compounds Having a Pharmacological Effect on Human or Mouse VLDL Receptor The highest level of expression of the VLDL receptor is found in the heart. The heart also synthesizes lipoprotein lipase (LPL) at a high level. VLDL receptor and LPL, acting- separately or in concert, mediate the uptake of lipids (VLDL and fatty acids) from the circulation. These lipids constitute a major source of energy for the heart. Disruption of VLDL receptor function will likely lead to cardiac dysfunction, such as congestive heart failure, cardiomyopathy or arrhythmia. By using wild-type human or mouse or variant human or mouse VLDL receptors expressed in vitro, we can screen for various natural and synthetic compounds that bind to the VLDL receptor (by a modification of the method of Goldstein et al., Methods Enzymol. 98: 241–260, 1983, using apoE-containing lipoproteins instead of LDL as a competing ligand). Compounds identified by in vitro binding experiments can be tested for metabolic effects in vitro, e.g., do they block or modulate VLDL uptake, or LPL action? Do they modulate HMGCOA reductase activity (by the method of Goldstein et al., Methods Enzymol. 98: 241–260, 1983)? The bioactive compounds can be tested in experimental animals in vivo. The compounds found to have beneficial therapeutic effects in congestive heart failure, cardiomyopathy or cardiac arrhythmia may ultimately be used as therapeutic agents in humans or animals.

EXAMPLE 6

Diagnostic Imaging Utilizing Human or Mouse VLDL Receptor

The high concentration of VLDL receptor in heart may provide a useful handle for developing in vivo diagnostic imaging equipment. Natural or synthetic ligands for this receptor can be labeled (e.g., with $^{125}$I or other radionuclides) and injected intravenously. The imaging and quantitation of the radionuclide uptake by the heart will allow the structure and function of the heart to be studied in vivo. The ligands in such studies include VLDL, apoE-containing vesicles, labeled monoclonal antibodies against the VLDL receptor, or other natural or synthetic compounds identified by in vitro binding assays. Labels which are detectable by magnetic resonance imaging, positron emission tomography or computerized axial tomography are also suitable.

EXAMPLE 7

Use of the Mouse VLDL Receptor

The mouse is a useful animal for both genetic and conventional therapy. It is especially useful for drug screening. The VLDL receptor nucleic acid sequence will be useful in this type of screening. Since the mouse VLDL receptor sequence is highly homologous to the human VLDL receptor, sharing over 95% sequence identity with the latter, many of the methods applicable to the mouse will be applicable to humans. All the uses of the human VLDL receptor discussed in the previous sections can be applied to the mouse VLDL receptor as well. In addition, natural or synthetic compounds that bind to the VLDL receptor, or that modulate VLDL receptor expression can be studied in mouse in vivo before they are used for clinical trials in humans.

EXAMPLE 8

In Vitro Uses of VLDL Nucleic Acid Sequences and Vectors

The human or mouse VLDL nucleic acid sequences or vectors containing such sequences can be used as probes, as is known in the art, in order to screen cDNA or genomic libraries and isolate additional VLDL receptors and/or other as yet unidentified lipoprotein receptors. The human or mouse VLDL nucleic acid sequences or vectors containing such sequences can also be utilized to perform in situ hybridizations, as is known in the art, in order to further characterize the tissue distribution of the VLDL receptor or homologous lipoprotein receptors in various species.

Stably transformed or transfected cell lines which express VLDL receptors are useful for the screening of compounds which will specifically bind to these VLDL receptors.

EXAMPLE 9

Isolation and Cloning of VLDL Receptor Genes

Nucleic acid sequences encoding VLDL receptor genes may be isolated and cloned as is known in the art, as set forth in, for example, Maniatis, Fritsch and Sambrook, Molecular Cloning: A Laboratory Manual, Cold Spring Harbor Laboratory, Cold Spring Harbor, N.Y. 1982.

Probes generated from LDL receptor nucleic acid sequences or VLDL receptor nucleic acid sequences as are known including rabbit, mouse and human may be used. For example, the human and mouse VLDL receptor genes were isolated utilizing probes based on the rabbit VLDL receptor sequence.

It will be readily apparent to one skilled in the art that various substitutions and modifications may be made to the invention disclosed herein without departing from the scope and spirit of the invention.

What is claimed is:

1. A method for detecting the presence of a human nucleic acid sequence encoding a Human Very Low Density Lipoprotein receptor or a subsequence or complement thereof that specifically hybridizes to said Human Very Low Density Lipoprotein receptor comprising the steps of:
   (a) obtaining a sample containing a human nucleic acid sequence encoding at least part of said human Very Low Density Lipoprotien receptor or said subsequence or said complement thereof in an amount sufficient for detection;
   (b) detecting said human nucleic acid sequence, wherein
   (c) said detection occurs using an oligonucleotide able to hybridize to said human nucleic acid sequence to form a detectable target:probe duplex under selective hybridization assay conditions, and
   (d) wherein said oligonucleotide does not hybridize to nucleic acid that does not encode said human very low density lipoprotein receptor or a subsequence or complement thereof to form a detectable non-target:probe duplex under said hybridization conditions.

2. The method of claim 1, wherein said selective hybridization assay conditions comprise the use of approximately 0.12M phosphate buffer containing equimolar amounts of $NaH_2PO_4$ and $NaH_2PO_4$, about 1 mM EDTA and approximately 0.02% sodium dodecyl sulfate at about 65° C.

3. A method for detecting the presence of a human nucleic acid sequence encoding a human Very Low Density Lipoprotein receptor or a subsequence or complement thereof that specifically hybridizes to said human Very Low Density Lipoprotein receptor comprising the steps of:
   a) obtaining a sample containing a human nucleic acid sequence encoding at least part of said human Very low Density Lipoprotein receptor or said subsequence or said complement thereof in an amount sufficient for detection;
   (b) detecting said human nucleic acid sequence wherein
   (c) said detection occurs using an oligonucleotide comprising the nucleic acid sequence set forth in SEQ ID NO: 1 or SEQ ID NO: 2 under selective hybridization assay conditions.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 3330 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
TTTCCCCTCC  CCGCCCCCAC  CTTCTTCCTC  CTTTCGGAAG  GGCTGGTAAC  TTGTCGTGCG    60

GAGCGAACGG  CGGCGGCGGC  GGCGGCGGCG  GCGGCACCAT  CCAGGCGGGC  ACCATGGGCA   120

CGTCCGCGCT  CTGGGCGCTC  TGGCTGCTCG  TCGCGCTGTG  CTGGGCGCCC  CGGGAGAGCG   180

GCGCCACCGG  AACCGGGAGA  AAAGCCAAAT  GTGAACCCTC  CCAATTCCAG  TGCACAAATG   240
```

-continued

| | | | | | |
|---|---|---|---|---|---|
| GTCGCTGTAT | TACGCTGTTG | TGGAAATGTG | ATGGGGATGA | AGACTGTGTT | GACGGCAGTG 300 |
| ATGAAAAGAA | CTGTGTAAAG | AAGACGTGTG | CTGAATCTGA | CTTCGTGTGC | AACAATGGCC 360 |
| AGTGTGTTCC | CAGCCGATGG | AAGTGTGATG | GAGATCCTGA | CTGCGAAGAT | GGTTCAGATG 420 |
| AAAGCCCAGA | ACAGTGCCAT | ATGAGAACAT | GCCGCATACA | TGAAATCAGC | TGTGGCGCCC 480 |
| ATTCTACTCA | GTGTATCCCA | GTGTCCTGGA | GATGTGATGG | TGAAAATGAT | TGTGACAGTG 540 |
| GAGAAGATGA | AGAAAACTGT | GGCAATATAA | CATGTAGTCC | CGACGAGTTC | ACCTGCTCCA 600 |
| GTGGCCGCTG | CATCTCCAGG | AACTTTGTAT | GCAATGGCCA | GGATGACTGC | AGCGATGGCA 660 |
| GTGATGAGCT | GGACTGTGCC | CCGCCAACCT | GTGGCGCCCA | TGAGTTCCAG | TGCAGCACCT 720 |
| CCTCCTGCAT | CCCCATCAGC | TGGGTATGCG | ACGATGATGC | AGACTGCTCC | GACCAATCTG 780 |
| ATGAGTCCCT | GGAGCAGTGT | GGCCGTCAGC | CAGTCATACA | CACCAAGTGT | CCAGCCAGCG 840 |
| AAATCCAGTG | CGGCTCTGGC | GAGTGCATCC | ATAAGAAGTG | GCGATGTGAT | GGGGACCCTG 900 |
| ACTGCAAGGA | TGGCAGTGAT | GAGGTCAACT | GTCCCTCTCG | AACTTGCCGA | CCTGACCAAT 960 |
| TTGAATGTGA | GGATGGCAGC | TGCATCCATG | GCAGCAGGCA | GTGTAATGGT | ATCCGAGACT 1020 |
| GTGTCGATGG | TTCCGATGAA | GTCAACTGCA | AAAATGTCAA | TCAGTGCTTG | GGCCCTGGAA 1080 |
| AATTCAAGTG | CAGAAGTGGA | GAATGCATAG | ATATCAGCAA | AGTATGTAAC | CAGGAGCAGG 1140 |
| ACTGCAGGGA | CTGGAGTGAT | GAGCCCCTGA | AGAGTGTCA | TATAAACGAA | TGCTTGGTAA 1200 |
| ATAATGGTGG | ATGTTCTCAT | ATCTGCAAAG | ACCTAGTTAT | AGGCTACGAG | TGTGACTGTG 1260 |
| CAGCTGGGTT | TGAACTGATA | GATAGGAAAA | CCTGTGGAGA | TATTGATGAA | TGCCAAAATC 1320 |
| CAGGAATCTG | CAGTCAAATT | TGTATCAACT | TAAAAGGCGG | TTACAAGTGT | GAATGTAGTC 1380 |
| GTGGCTATCA | AATGGATCTT | GCTACTGGCG | TGTGCAAGGC | AGTAGGCAAA | GAGCCAAGTC 1440 |
| TGATCTTCAC | TAATCGAAGA | GACATCAGGA | AGATTGGCTT | AGAGAGGAAA | GAATATATCC 1500 |
| AACTAGTTGA | ACAGCTAAGA | AACACTGTGG | CTCTCGATGC | TGACATTGCT | GCCCAGAAAC 1560 |
| TATTCTGGGC | CGATCTAAGC | CAAAAGGCTA | TCTTCAGTGC | CTCAATTGAT | GACAAGGTTG 1620 |
| GTAGACATGT | TAAAATGATC | GACAATGTCT | ATAATCCTGC | AGCCATTGCT | GTTGATTGGG 1680 |
| TGTACAAGAC | CATCTACTGG | ACTGATGCGG | CTTCTAAGAC | TATTTCAGTA | GCTACCCTAG 1740 |
| ATGGAACCAA | GAGGAAGTTC | CTGTTTAACT | CTGACTTGCG | AGAGCCTGCC | TCCATAGCTG 1800 |
| TGGACCCACT | GTCTGGCTTT | GTTACTGGT | CAGACTGGGG | TGAACCAGCT | AAAATAGAAA 1860 |
| AAGCAGGAAT | GAATGGATTC | GATAGACGTC | CACTGGTGAC | AGCGGATATC | CAGTGGCCTA 1920 |
| ACGGAATTAC | ACTTGACCTT | ATAAAAGTC | GCCTCTATTG | GCTTGATTCT | AAGTTGCACA 1980 |
| TGTTATCCAG | CGTGGACTTG | AATGGCCAAG | ATCGTAGGAT | AGTACTAAAG | TCTCTGGAGT 2040 |
| TCCTAGCTCA | TCCTCTTGCA | CTAACAATAT | TTGAGGATCG | TGTCTACTGG | ATAGATGGGG 2100 |
| AAAATGAAGC | AGTCTATGGT | GCCAATAAAT | TCACTGGATC | AGAGCTAGCC | ACTCTAGTCA 2160 |
| ACAACCTGAA | TGATGCCCAA | GACATCATTG | TCTATCATGA | ACTTGTACAG | CCATCAGGTA 2220 |
| AAAATTGGTG | TGAAGAAGAC | ATGGAGAATG | GAGGATGTGA | ATACCTATGC | CTGCCAGCAC 2280 |
| CACAGATTAA | TGATCACTCT | CCAAAATATA | CCTGTTCCTG | TCCCAGTGGG | TACAATGTAG 2340 |
| AGGAAAATGG | CCGAGACTGT | CAAAGTACTG | CAACTACTGT | GACTTACAGT | GAGACAAAAG 2400 |
| ATACGAACTC | AACAGAAATT | TCAGCAACTA | GTGGACTAGT | TCCTGGAGGG | ATCAATGTGA 2460 |
| CCACAGCAGT | ATCAGAGGTC | AGTGTTCCCC | CAAAAGGGAC | TTCTGCCGCA | TGGGCCATTC 2520 |
| TTCCTCTCTT | GCTCTTAGTG | ATGGCAGCAG | TAGGTGGCTA | CTTGATGTGG | CGGAATTGGC 2580 |
| AACACAAGAA | CATGAAAAGC | ATGAACTTTG | ACAATCCTGT | GTACTTGAAA | ACCACTGAAG 2640 |

-continued

```
AGGACCTCTC  CATAGACATT  GGTAGACACA  GTGCTTCTGT  TGGACACACG  TACCCAGCAA    2700

TATCAGTTGT  AAGCACAGAT  GATGATCTAG  CTTGACTTCT  GTGACAAATG  TTGACCTTTG    2760

AGGTCTAAAC  AAATAATACC  CCCGTCGGAA  TGGTAACCGA  GCCAGCAGCT  GAAGTCTCTT    2820

TTTCTTCCTC  TCGGCTGGAA  GAACATCAAG  ATACCTTTGC  GTGGATCAAG  CTTGTGTACT    2880

TGACCGTTTT  TATATTACTT  TTGTAAATAT  TCTTGTCCAC  ATTCTACTTC  AGCTTTGGAT    2940

GTGGTTACCG  AGTATCTGTA  ACCCTTGAAT  TTCTAGACAG  TATTGCCACC  TCTGGCCAAA    3000

TATGCACTTT  CCCTAGAAAG  CCATATTCCA  GCAGTGAAAC  TTGTGCTATA  GTGTATACCA    3060

CCTGTACATA  CATTGTATAG  GCCATCTGTA  AATATCCCAG  AGAACAATCA  CTATTCTTAA    3120

GCACTTTGAA  AATATTTCTA  TGTAAATTAT  TGTAAACTTT  TTCAATGGTT  GGGACAATGG    3180

CAATAGGACA  AAACGGGTTA  CTAAGATGAA  ATTGCCAAAA  AAATTTATAA  ACTAATTTTG    3240

TACGTATGAA  TGATATCTTT  GACCTCAATG  GAGGTTTGCA  AAGACTGAGT  GTTCAAACTA    3300

CTGTACATTT  TTTTCAAGT   GCTAAAAAT                                        3330
```

( 2 ) INFORMATION FOR SEQ ID NO: 2:

( i ) SEQUENCE CHARACTERISTICS:
( A ) LENGTH: 3116 base pairs
( B ) TYPE: nucleic acid
( C ) STRANDEDNESS: single
( D ) TOPOLOGY: linear ( x i ) SEQUENCE DESCRIPTION: SEQ ID NO: 2:

```
CACCATCCGG  GCGGGCAGCA  TGGGCACGTC  CGCGCGCTGG  GCCCTGTGGC  TGCTGCTCGC     60

GCTGTGCTGG  GCGCCCCGGG  ACAGCGGCGC  CACTGCAAGC  GGGAAGAAAG  CCAAATGTGA    120

TAGCTCCCAG  TTTCAGTGCA  CAAATGGCCG  CTGCATTACC  CTGCTGTGGA  AATGTGATGG    180

AGATGAAGAC  TGTGCGGATG  GCAGCGACGA  GAAGAACTGT  GTAAAGAAGA  CGTGTGCTGA    240

GTCTGACTTC  GTGTGCAAAA  ACGGCCAGTG  TGTTCCTAAC  AGATGGCAGT  GTGACGGGGA    300

TCCTGATTGC  GAAAACGGTT  CTGATGAAAG  CCCTGAACAG  TGCCATATGA  ACATGCCG     360

CATAAATGAA  ATCAGCTGTG  GCGCCCGTTC  TACTCAGTGT  ATCCCCGTCT  CCTGGAGATG    420

CGATGGTGAA  AATGATTGTG  ACAATGGAGA  AGATGAAGAA  AACTGTGGCA  ACATAACATG    480

TAGTGCAGAT  GAGTTCACTT  GCTCCAGTGG  CCGCTGCGTC  TCCAGAAACT  TTGTGTGCAA    540

TGGCCAGGAT  GACTGTGACG  ATGGCAGTGA  TGAGCTGGAC  TGTGCTCCAC  CAACCTGCGG    600

AGCCCACGAG  TTCCAGTGCA  GCACCTCTTC  CTGCATTCCC  CTCAGCTGGG  TGTGTGATGA    660

TGACGCAGAC  TGTTCAGACC  AATCAGACGA  GTCTCTTGAG  CAGTGTGGCC  GTCAGCCTGT    720

GATACATACC  AAATGTCCTA  CCAGTGAGAT  CCAGTGTGGC  TCTGGCGAGT  GCATTCACAA    780

AAAATGGCGG  TGTGACGGAG  ACCCTGACTG  CAAGGACGGC  AGCGATGAGG  TCAACTGCCC    840

TTCTCGAACC  TGCCGACCTG  ACCAGTTTGA  ATGTGAAGAT  GGTAGCTGTA  TCCACGGCAG    900

CAGGCAATGC  AATGGCATCC  GAGACTGTGT  TGATGGCTCT  GATGAAGTCA  ACTGCAAAAA    960

CGTCAATCAG  TGCCTGGGCC  CTGGAAAGTT  CAAGTGCAGA  AGCGGGGAAT  GCATAGACAT    1020

GAGCAAAGTA  TGTGACCAGG  AACAAGACTG  CAGAGACTGG  AGTGACGAGC  CCCTGAAGGA    1080

ATGCCATATC  AACGAATGCC  TGGTCAATAA  TGGTGGCTGT  TCCCATATCT  GCAAAGACCT    1140

AGTTATAGGT  TATGAGTGTG  ATTGTGCAGC  TGGGTTTGAA  CTGATAGATA  GGAAAACCTG    1200

TGGAGATATT  GATGAATGCC  AAAACCCGGG  GATCTGCAGT  CAAATTTGTA  TCAACTTAAA    1260

AGGCGGTTAC  AAGTGTGAAT  GTAGTCGTGG  CTATCAAATG  GATCTTGCCA  CTGGCGTGTG    1320

CAAGGCAGTA  GGCAAAGAGC  CGAGTCTGAT  CTTCACTAAT  CGAAGAGACA  TCAGGAAGAT    1380
```

| | | | | | |
|---|---|---|---|---|---|
| TGGCCTAGAG | AGAAAGGAAT | ACATCCAACT | TGTAGAGCAA | CTAAGGAACA | CGGTGGCTCT | 1440
| CGATGCGGAC | ATTGCAGCTC | AGAAGCTGTT | TTGGGCTGAT | CTCAGCCAGA | AGGCCATCTT | 1500
| CAGTGCCTCA | ATTGATGACA | AGGTTGGTAG | ACATTTTAAA | ATGATCGACA | ATGTCTATAA | 1560
| TCCTGCAGCC | ATTGCTGTTG | ATTGGGTGTA | CAAGACCATC | TACTGGACTG | ATGCGGCTTC | 1620
| TAAGACTATT | TCAGTAGCTA | CCCTAGACGG | AGCCAAGAGG | AAGTTCCTGT | TTAATTCTGA | 1680
| CTTGCGAGAG | CCTGCCTCCA | TAGCTGTGGA | TCCGTTGTCG | GGCTTTGTTT | ACTGGTCAGA | 1740
| CTGGGGCGAG | CCAGCTAAAA | TAGAAAAAGC | AGGAATGAAT | GGATTTGATA | GACGTCCTCT | 1800
| GGTGACGGAG | GACATCCAAT | GGCCTAATGG | AATTACACTC | GACCTTGTCA | AAAGCCGCCT | 1860
| CTACTGGCTG | GATTCCAAGT | TGCACATGCT | CTCTAGTGTG | GACCTGAATG | GTCAAGATCG | 1920
| TAGGATAGTG | CTCAAGTCTC | TGGAGTTCCT | AGCTCATCCT | CTTGCACTCA | CCATATTTGA | 1980
| GGATCGCGTC | TACTGGATAG | ATGGAGAAAA | TGAAGCAGTG | TACGGTGCCA | ATAAATTCAC | 2040
| TGGGTCAGAG | CTGGCCACTC | TAGTGAATTC | CCTCAATGAT | GCCCAAGACA | TCATTGTCTA | 2100
| CCATGAACTC | GTCCAGCCGT | CAGGTAAAAA | CTGGTGTGAA | GACGATATGG | AGAATGGAGG | 2160
| ATGTGAATAT | CTCTGCCTGC | CAGCACCACA | GATCAATGAC | CACTCTCCAA | AATATACCTG | 2220
| TTCCTGTCCC | AATGGGTACA | ATCTCGAAGA | AAATGGACGA | GAGTGTCAAA | GTACTTCAAC | 2280
| TCCTGTGACT | TACAGTGAGA | CAAAAGATAT | CAACACAACA | GACATTCTAC | GAACTAGTGG | 2340
| ACTGGTTCCT | GGAGGGATCA | ATGTGACCAC | AGCAGTATCA | GAAGTCAGTG | TTCCCCCAAA | 2400
| AGGGACTTCA | GCTGCCTGGG | CCATCCTTCC | TCTCTTGCTC | TTAGTGATGG | CAGCAGTAGG | 2460
| TGGCTACTTG | ATGTGGAGGA | ATTGGCAACA | TAAAAACATG | AAAAGCATGA | ACTTTGACAA | 2520
| TCCTGTGTAC | TTGAAGACCA | CTGAAGAGGA | CCTGTCGATA | GACATTGGTA | GACACAGCGC | 2580
| TTCTGTAGGA | CACACATACC | CAGCAATATC | AGTTGTAAGC | ACAGATGATG | ATCTGGCTTG | 2640
| AGTTCTGAAC | AAATCTTGGT | CTATGAGGTC | TACACCAATA | ACACCCTACT | CTGGAATGGT | 2700
| AACAGAGCCA | GCGCTGAAGT | CTCCTTTCTT | CCTCCCATCT | GGAAGAACAT | CAAGATATCT | 2760
| TTTTGTGGAT | CAAGTTTGAG | TACTTGATCA | TTTTTATATT | ACTTTTGTAA | ATATTCTTGG | 2820
| CCACATTCTA | CTTCAGCTCT | GGATGTGGTT | ACCAAGTATC | TGTAACCCTT | GAGCCCCTAG | 2880
| ACAGTATTGC | CATCTCTGGC | CAAATATGCA | CTTTCCCTAG | AAAGCCATAT | TCCAGCAATG | 2940
| AACGTTGTGC | TATAGTGACT | CCCACCTGTA | CATACATTGT | ATAGGCCACC | TGTACATATC | 3000
| CCAGAGAACA | ATCACTATTC | TTAAGCACTT | TGAAGATATT | TCTATGTAAA | TTATTGTAAA | 3060
| CTTTTTCAAT | GGTTGGGACA | ATGGCAATAG | GATAAAACGG | GTTACTAAGA | TGAAAT | 3116

( 2 ) INFORMATION FOR SEQ ID NO: 3:

( i ) SEQUENCE CHARACTERISTICS:
        ( A ) LENGTH: 846 amino acids
        ( B ) TYPE: amino acid
        ( C ) STRANDEDNESS: single
        ( D ) TOPOLOGY: linear ( x i ) SEQUENCE DESCRIPTION: SEQ ID NO: 3:

```
Gly Arg Lys Ala Lys Cys Glu Pro Ser Gln Phe Gln Cys Thr Asn Gly
  1               5                  10                  15

Arg Cys Ile Thr Leu Leu Trp Lys Cys Asp Gly Asp Glu Asp Cys Val
             20                  25                  30

Asp Gly Ser Asp Glu Lys Asn Cys Val Lys Lys Thr Cys Ala Glu Ser
         35                  40                  45

Asp Phe Val Cys Asn Asn Gly Gln Cys Val Pro Ser Arg Trp Lys Cys
```

|   |   |   |   | 50 |   |   |   | 55 |   |   |   | 60 |   |   |   |
|---|---|---|---|---|---|---|---|---|---|---|---|---|---|---|---|
| Asp | Gly | Asp | Pro | Asp | Cys | Glu | Asp | Gly | Ser | Asp | Glu | Ser | Pro | Glu | Gln |
| 65 |   |   |   | 70 |   |   |   | 75 |   |   |   |   |   |   | 80 |
| Cys | His | Met | Arg | Thr | Cys | Arg | Ile | His | Glu | Ile | Ser | Cys | Gly | Ala | His |
|   |   |   |   | 85 |   |   |   |   | 90 |   |   |   |   | 95 |   |
| Ser | Thr | Gln | Cys | Ile | Pro | Val | Ser | Trp | Arg | Cys | Asp | Gly | Glu | Asn | Asp |
|   |   |   | 100 |   |   |   |   | 105 |   |   |   |   | 110 |   |   |
| Cys | Asp | Ser | Gly | Glu | Asp | Glu | Asn | Cys | Gly | Asn | Ile | Thr | Cys | Ser |   |
|   |   | 115 |   |   |   |   | 120 |   |   |   | 125 |   |   |   |   |
| Pro | Asp | Glu | Phe | Thr | Cys | Ser | Ser | Gly | Arg | Cys | Ile | Ser | Arg | Asn | Phe |
|   | 130 |   |   |   |   | 135 |   |   |   | 140 |   |   |   |   |   |
| Val | Cys | Asn | Gly | Gln | Asp | Asp | Cys | Ser | Asp | Gly | Ser | Asp | Glu | Leu | Asp |
| 145 |   |   |   |   | 150 |   |   |   | 155 |   |   |   |   |   | 160 |
| Cys | Ala | Pro | Pro | Thr | Cys | Gly | Ala | His | Glu | Phe | Gln | Cys | Ser | Thr | Ser |
|   |   |   |   | 165 |   |   |   |   | 170 |   |   |   |   | 175 |   |
| Ser | Cys | Ile | Pro | Ile | Ser | Trp | Val | Cys | Asp | Asp | Ala | Asp | Cys | Ser |   |
|   |   |   | 180 |   |   |   |   | 185 |   |   |   | 190 |   |   |   |
| Asp | Gln | Ser | Asp | Glu | Ser | Leu | Glu | Gln | Cys | Gly | Arg | Gln | Pro | Val | Ile |
|   |   | 195 |   |   |   |   | 200 |   |   |   |   | 205 |   |   |   |
| His | Thr | Lys | Cys | Pro | Ala | Ser | Glu | Ile | Gln | Cys | Gly | Ser | Gly | Glu | Cys |
|   | 210 |   |   |   |   | 215 |   |   |   |   | 220 |   |   |   |   |
| Ile | His | Lys | Lys | Trp | Arg | Cys | Asp | Gly | Asp | Pro | Asp | Cys | Lys | Asp | Gly |
| 225 |   |   |   |   | 230 |   |   |   |   | 235 |   |   |   |   | 240 |
| Ser | Asp | Glu | Val | Asn | Cys | Pro | Ser | Arg | Thr | Cys | Arg | Pro | Asp | Gln | Phe |
|   |   |   |   | 245 |   |   |   |   | 250 |   |   |   |   | 255 |   |
| Glu | Cys | Glu | Asp | Gly | Ser | Cys | Ile | His | Gly | Ser | Arg | Gln | Cys | Asn | Gly |
|   |   |   | 260 |   |   |   |   | 265 |   |   |   |   | 270 |   |   |
| Ile | Arg | Asp | Cys | Val | Asp | Gly | Ser | Asp | Glu | Val | Asn | Cys | Lys | Asn | Val |
|   |   | 275 |   |   |   |   | 280 |   |   |   |   | 285 |   |   |   |
| Asn | Gln | Cys | Leu | Gly | Pro | Gly | Lys | Phe | Lys | Cys | Arg | Ser | Gly | Glu | Cys |
|   | 290 |   |   |   |   | 295 |   |   |   |   | 300 |   |   |   |   |
| Ile | Asp | Ile | Ser | Lys | Val | Cys | Asn | Gln | Glu | Gln | Asp | Cys | Arg | Asp | Trp |
| 305 |   |   |   |   | 310 |   |   |   |   | 315 |   |   |   |   | 320 |
| Ser | Asp | Glu | Pro | Leu | Lys | Glu | Cys | His | Ile | Asn | Glu | Cys | Leu | Val | Asn |
|   |   |   |   | 325 |   |   |   |   | 330 |   |   |   |   | 335 |   |
| Asn | Gly | Gly | Cys | Ser | His | Ile | Cys | Lys | Asp | Leu | Val | Ile | Gly | Tyr | Glu |
|   |   |   | 340 |   |   |   |   | 345 |   |   |   |   | 350 |   |   |
| Cys | Asp | Cys | Ala | Ala | Gly | Phe | Glu | Leu | Ile | Asp | Arg | Lys | Thr | Cys | Gly |
|   |   | 355 |   |   |   |   | 360 |   |   |   |   | 365 |   |   |   |
| Asp | Ile | Asp | Glu | Cys | Gln | Asn | Pro | Gly | Ile | Cys | Ser | Gln | Ile | Cys | Ile |
|   | 370 |   |   |   |   | 375 |   |   |   |   | 380 |   |   |   |   |
| Asn | Leu | Lys | Gly | Gly | Tyr | Lys | Cys | Glu | Cys | Ser | Arg | Gly | Tyr | Gln | Met |
| 385 |   |   |   |   | 390 |   |   |   |   | 395 |   |   |   |   | 400 |
| Asp | Leu | Ala | Thr | Gly | Val | Cys | Lys | Ala | Val | Gly | Lys | Glu | Pro | Ser | Leu |
|   |   |   |   | 405 |   |   |   |   | 410 |   |   |   |   | 415 |   |
| Ile | Phe | Thr | Asn | Arg | Arg | Asp | Ile | Arg | Lys | Ile | Gly | Leu | Glu | Arg | Lys |
|   |   |   | 420 |   |   |   |   | 425 |   |   |   |   | 430 |   |   |
| Glu | Tyr | Ile | Gln | Leu | Val | Glu | Gln | Leu | Arg | Asn | Thr | Val | Ala | Leu | Asp |
|   |   | 435 |   |   |   |   | 440 |   |   |   |   | 445 |   |   |   |
| Ala | Asp | Ile | Ala | Ala | Gln | Lys | Leu | Phe | Trp | Ala | Asp | Leu | Ser | Gln | Lys |
|   | 450 |   |   |   |   | 455 |   |   |   |   | 460 |   |   |   |   |
| Ala | Ile | Phe | Ser | Ala | Ser | Ile | Asp | Asp | Lys | Val | Gly | Arg | His | Val | Lys |
| 465 |   |   |   |   | 470 |   |   |   |   | 475 |   |   |   |   | 480 |

| | | | | | | | | | | | | | | |
|---|---|---|---|---|---|---|---|---|---|---|---|---|---|---|
| Met | Ile | Asp | Asn | Val<br>485 | Tyr | Asn | Pro | Ala | Ala<br>490 | Ile | Ala | Val | Asp | Trp<br>495 | Val |
| Tyr | Lys | Thr | Ile<br>500 | Tyr | Trp | Thr | Asp | Ala<br>505 | Ala | Ser | Lys | Thr | Ile<br>510 | Ser | Val |
| Ala | Thr | Leu<br>515 | Asp | Gly | Thr | Lys | Arg<br>520 | Lys | Phe | Leu | Phe | Asn<br>525 | Ser | Asp | Leu |
| Arg | Glu<br>530 | Pro | Ala | Ser | Ile<br>535 | Ala | Val | Asp | Pro | Leu<br>540 | Ser | Gly | Phe | Val | Tyr |
| Trp<br>545 | Ser | Asp | Trp | Gly | Glu<br>550 | Pro | Ala | Lys | Ile<br>555 | Glu | Lys | Ala | Gly | Met | Asn<br>560 |
| Gly | Phe | Asp | Arg | Arg<br>565 | Pro | Leu | Val | Thr | Ala<br>570 | Asp | Ile | Gln | Trp | Pro<br>575 | Asn |
| Gly | Ile | Thr | Leu<br>580 | Asp | Leu | Ile | Lys | Ser<br>585 | Arg | Leu | Tyr | Trp | Leu<br>590 | Asp | Ser |
| Lys | Leu | His<br>595 | Met | Leu | Ser | Ser | Val<br>600 | Asp | Leu | Asn | Gly | Gln<br>605 | Asp | Arg | Arg |
| Ile | Val<br>610 | Leu | Lys | Ser | Leu | Glu<br>615 | Phe | Leu | Ala | His | Pro<br>620 | Leu | Ala | Leu | Thr |
| Ile<br>625 | Phe | Glu | Asp | Arg | Val<br>630 | Tyr | Trp | Ile | Asp | Gly<br>635 | Glu | Asn | Glu | Ala | Val<br>640 |
| Tyr | Gly | Ala | Asn | Lys<br>645 | Phe | Thr | Gly | Ser | Glu<br>650 | Leu | Ala | Thr | Leu | Val<br>655 | Asn |
| Asn | Leu | Asn | Asp<br>660 | Ala | Gln | Asp | Ile | Ile<br>665 | Val | Tyr | His | Glu | Leu<br>670 | Val | Gln |
| Pro | Ser | Gly<br>675 | Lys | Asn | Trp | Cys | Glu<br>680 | Glu | Asp | Met | Glu | Asn<br>685 | Gly | Gly | Cys |
| Glu | Tyr<br>690 | Leu | Cys | Leu | Pro | Ala<br>695 | Pro | Gln | Ile | Asn | Asp<br>700 | His | Ser | Pro | Lys |
| Tyr<br>705 | Thr | Cys | Ser | Cys | Pro<br>710 | Ser | Gly | Tyr | Asn | Val<br>715 | Glu | Glu | Asn | Gly | Arg<br>720 |
| Asp | Cys | Gln | Ser | Thr<br>725 | Ala | Thr | Thr | Val | Thr<br>730 | Tyr | Ser | Glu | Thr | Lys<br>735 | Asp |
| Thr | Asn | Ser | Thr<br>740 | Glu | Ile | Ser | Ala | Thr<br>745 | Ser | Gly | Leu | Val | Pro<br>750 | Gly | Gly |
| Ile | Asn | Val<br>755 | Thr | Thr | Ala | Val | Ser<br>760 | Glu | Val | Ser | Val | Pro<br>765 | Pro | Lys | Gly |
| Thr | Ser<br>770 | Ala | Ala | Trp | Ala | Ile<br>775 | Leu | Pro | Leu | Leu | Leu<br>780 | Leu | Val | Met | Ala |
| Ala<br>785 | Val | Gly | Gly | Tyr | Leu<br>790 | Met | Trp | Arg | Asn | Trp<br>795 | Gln | His | Lys | Asn | Met<br>800 |
| Lys | Ser | Met | Asn | Phe<br>805 | Asp | Asn | Pro | Val | Tyr<br>810 | Leu | Lys | Thr | Thr | Glu<br>815 | Glu |
| Asp | Leu | Ser | Ile<br>820 | Asp | Ile | Gly | Arg | His<br>825 | Ser | Ala | Ser | Val | Gly<br>830 | His | Thr |
| Tyr | Pro | Ala<br>835 | Ile | Ser | Val | Val | Ser<br>840 | Thr | Asp | Asp | Asp | Leu<br>845 | Ala | | |

( 2 ) INFORMATION FOR SEQ ID NO: 4:

( i ) SEQUENCE CHARACTERISTICS:
        ( A ) LENGTH: 846 amino acids
        ( B ) TYPE: amino acid
        ( C ) STRANDEDNESS: single
        ( D ) TOPOLOGY: linear ( x i ) SEQUENCE DESCRIPTION: SEQ ID NO: 4:

-continued

```
Gly Lys Lys Ala Lys Cys Asp Ser Ser Gln Phe Gln Cys Thr Asn Gly
 1           5                   10                  15
Arg Cys Ile Thr Leu Leu Trp Lys Cys Asp Gly Asp Glu Asp Cys Ala
            20                  25              30
Asp Gly Ser Asp Glu Lys Asn Cys Val Lys Thr Cys Ala Glu Ser
            35                  40              45
Asp Phe Val Cys Lys Asn Gly Gln Cys Val Pro Asn Arg Trp Gln Cys
    50              55                  60
Asp Gly Asp Pro Asp Cys Glu Asn Gly Ser Asp Glu Ser Pro Glu Gln
 65             70              75                      80
Cys His Met Arg Thr Cys Arg Ile Asn Glu Ile Ser Cys Gly Ala Arg
                85              90              95
Ser Thr Gln Cys Ile Pro Val Ser Trp Arg Cys Asp Gly Glu Asn Asp
                100             105             110
Cys Asp Asn Gly Glu Asp Glu Glu Asn Cys Gly Asn Ile Thr Cys Ser
            115             120                 125
Ala Asp Glu Phe Thr Cys Ser Ser Gly Arg Cys Val Ser Arg Asn Phe
    130                 135                 140
Val Cys Asn Gly Gln Asp Asp Cys Asp Asp Gly Ser Asp Glu Leu Asp
145                 150             155                 160
Cys Ala Pro Pro Thr Cys Gly Ala His Glu Phe Gln Cys Ser Thr Ser
                165             170                 175
Ser Cys Ile Pro Leu Ser Trp Val Cys Asp Asp Ala Asp Cys Ser
            180                 185                 190
Asp Gln Ser Asp Glu Ser Leu Glu Gln Cys Gly Arg Gln Pro Val Ile
        195             200                 205
His Thr Lys Cys Pro Thr Ser Glu Ile Gln Cys Gly Ser Gly Glu Cys
210                 215                 220
Ile His Lys Lys Trp Arg Cys Asp Gly Asp Pro Asp Cys Lys Asp Gly
225             230                 235                 240
Ser Asp Glu Val Asn Cys Pro Ser Arg Thr Cys Arg Pro Asp Gln Phe
            245                 250                 255
Glu Cys Glu Asp Gly Ser Cys Ile His Gly Ser Arg Gln Cys Asn Gly
        260                 265                 270
Ile Arg Asp Cys Val Asp Gly Ser Asp Glu Val Asn Cys Lys Asn Val
        275                 280                 285
Asn Gln Cys Leu Gly Pro Gly Lys Phe Lys Cys Arg Ser Gly Glu Cys
290                 295                 300
Ile Asp Met Ser Lys Val Cys Asp Gln Glu Gln Asp Cys Arg Asp Trp
305             310                 315                 320
Ser Asp Glu Pro Leu Lys Glu Cys His Ile Asn Glu Cys Leu Val Asn
                325                 330                 335
Asn Gly Gly Cys Ser His Ile Cys Lys Asp Leu Val Ile Gly Tyr Glu
            340                 345                 350
Cys Asp Cys Ala Ala Gly Phe Glu Leu Ile Asp Arg Lys Thr Cys Gly
        355                 360                 365
Asp Ile Asp Glu Cys Gln Asn Pro Gly Ile Cys Ser Gln Ile Cys Ile
    370                 375                 380
Asn Leu Lys Gly Gly Tyr Lys Cys Glu Cys Ser Arg Gly Tyr Gln Met
385                 390                 395                 400
Asp Leu Ala Thr Gly Val Cys Lys Ala Val Gly Lys Glu Pro Ser Leu
                405                 410                 415
Ile Phe Thr Asn Arg Arg Asp Ile Arg Lys Ile Gly Leu Glu Arg Lys
                420                 425                 430
```

```
Glu  Tyr  Ile  Gln  Leu  Val  Glu  Gln  Leu  Arg  Asn  Thr  Val  Ala  Leu  Asp
          435                      440                     445

Ala  Asp  Ile  Ala  Ala  Gln  Lys  Leu  Phe  Trp  Ala  Asp  Leu  Ser  Gln  Lys
     450                      455                     460

Ala  Ile  Phe  Ser  Ala  Ser  Ile  Asp  Asp  Lys  Val  Gly  Arg  His  Phe  Lys
465                      470                     475                          480

Met  Ile  Asp  Asn  Val  Tyr  Asn  Pro  Ala  Ala  Ile  Ala  Val  Asp  Trp  Val
               485                      490                          495

Tyr  Lys  Thr  Ile  Tyr  Trp  Thr  Asp  Ala  Ala  Ser  Lys  Thr  Ile  Ser  Val
               500                      505                     510

Ala  Thr  Leu  Asp  Gly  Ala  Lys  Arg  Lys  Phe  Leu  Phe  Asn  Ser  Asp  Leu
          515                      520                     525

Arg  Glu  Pro  Ala  Ser  Ile  Ala  Val  Asp  Pro  Leu  Ser  Gly  Phe  Val  Tyr
     530                      535                     540

Trp  Ser  Asp  Trp  Gly  Glu  Pro  Ala  Lys  Ile  Glu  Lys  Ala  Gly  Met  Asn
545                      550                     555                          560

Gly  Phe  Asp  Arg  Arg  Pro  Leu  Val  Thr  Glu  Asp  Ile  Gln  Trp  Pro  Asn
               565                      570                          575

Gly  Ile  Thr  Leu  Asp  Leu  Val  Lys  Ser  Arg  Leu  Tyr  Trp  Leu  Asp  Ser
               580                      585                     590

Lys  Leu  His  Met  Leu  Ser  Ser  Val  Asp  Leu  Asn  Gly  Gln  Asp  Arg  Arg
          595                      600                     605

Ile  Val  Leu  Lys  Ser  Leu  Glu  Phe  Leu  Ala  His  Pro  Leu  Ala  Leu  Thr
     610                      615                     620

Ile  Phe  Glu  Asp  Arg  Val  Tyr  Trp  Ile  Asp  Gly  Glu  Asn  Glu  Ala  Val
625                      630                     635                          640

Tyr  Gly  Ala  Asn  Lys  Phe  Thr  Gly  Ser  Glu  Leu  Ala  Thr  Leu  Val  Asn
               645                      650                          655

Ser  Leu  Asn  Asp  Ala  Gln  Asp  Ile  Ile  Val  Tyr  His  Glu  Leu  Val  Gln
               660                      665                     670

Pro  Ser  Gly  Lys  Asn  Trp  Cys  Glu  Asp  Asp  Met  Glu  Asn  Gly  Gly  Cys
          675                      680                     685

Glu  Tyr  Leu  Cys  Leu  Pro  Ala  Pro  Gln  Ile  Asn  Asp  His  Ser  Pro  Lys
     690                      695                     700

Tyr  Thr  Cys  Ser  Cys  Pro  Asn  Gly  Tyr  Asn  Leu  Glu  Glu  Asn  Gly  Arg
705                      710                     715                          720

Glu  Cys  Gln  Ser  Thr  Ser  Thr  Pro  Val  Thr  Tyr  Ser  Glu  Thr  Lys  Asp
               725                      730                          735

Ile  Asn  Thr  Thr  Asp  Ile  Leu  Arg  Thr  Ser  Gly  Leu  Val  Pro  Gly  Gly
               740                      745                     750

Ile  Asn  Val  Thr  Thr  Ala  Val  Ser  Glu  Val  Ser  Val  Pro  Pro  Lys  Gly
          755                      760                     765

Thr  Ser  Ala  Ala  Trp  Ala  Ile  Leu  Pro  Leu  Leu  Leu  Leu  Val  Met  Ala
     770                      775                     780

Ala  Val  Gly  Gly  Tyr  Leu  Met  Trp  Arg  Asn  Trp  Gln  His  Lys  Asn  Met
785                      790                     795                          800

Lys  Ser  Met  Asn  Phe  Asp  Asn  Pro  Val  Tyr  Leu  Lys  Thr  Thr  Glu  Glu
               805                      810                          815

Asp  Leu  Ser  Ile  Asp  Ile  Gly  Arg  His  Ser  Ala  Ser  Val  Gly  His  Thr
               820                      825                     830

Tyr  Pro  Ala  Ile  Ser  Val  Val  Ser  Thr  Asp  Asp  Leu  Ala
          835                      840                     845
```